US007550279B2

(12) United States Patent
Nickel

(10) Patent No.: US 7,550,279 B2
(45) Date of Patent: Jun. 23, 2009

(54) AMYLOSE AND AMYLOPECTIN DERIVATIVES

(76) Inventor: Gary B. Nickel, 4050 Kennedy Drive East, Windsor, Ontario (CA) R9G 1X8

( * ) Notice: Subject to any disclaimer, the term of this patent is extended or adjusted under 35 U.S.C. 154(b) by 273 days.

(21) Appl. No.: 10/902,019

(22) Filed: Jul. 30, 2004

(65) Prior Publication Data

US 2005/0069992 A1 Mar. 31, 2005

Related U.S. Application Data

(60) Provisional application No. 60/490,905, filed on Jul. 30, 2003.

(51) Int. Cl.
*C12P 1/04* (2006.01)
*C12P 7/00* (2006.01)
(52) U.S. Cl. .................... 435/170; 435/68.1; 435/132; 424/93.46
(58) Field of Classification Search .............. 424/94.61, 424/93.46; 435/202, 170, 68.1, 132
See application file for complete search history.

(56) References Cited

U.S. PATENT DOCUMENTS

| | | | |
|---|---|---|---|
| 2,557,091 A | 6/1951 | Gamrath et al. ............ 260/30.6 |
| 2,876,160 A | 3/1959 | Schoch et al. ................. 167/82 |
| 3,839,320 A | 10/1974 | Bauer ...................... 260/233.5 |
| 3,974,034 A | 8/1976 | Horn et al. ..................... 195/31 |
| 4,048,435 A | 9/1977 | Rutenberg et al. .......... 536/106 |
| 4,192,783 A | 3/1980 | Bomball et al. ................ 260/8 |
| 4,499,116 A | 2/1985 | Zwiercan et al. ............ 426/582 |
| 4,501,888 A | 2/1985 | Schmidt ...................... 536/110 |
| 4,510,166 A | 4/1985 | Lenchin et al. ............. 426/565 |
| 4,608,265 A | 8/1986 | Zwiercan et al. ............ 426/582 |
| 4,695,475 A | 9/1987 | Zwiercan et al. ............ 426/582 |
| 4,840,807 A | 6/1989 | Yoshida et al. ................ 426/48 |
| 4,937,091 A | 6/1990 | Zallie et al. ................. 426/582 |
| 4,971,723 A | 11/1990 | Chiu ........................ 252/315.3 |
| 4,977,252 A | 12/1990 | Chiu ........................... 536/102 |
| 5,164,215 A | 11/1992 | Furcsik et al. .............. 426/549 |
| 5,185,176 A | 2/1993 | Chiu ........................... 426/651 |
| 5,200,216 A | 4/1993 | Barz et al. ..................... 426/36 |
| 5,244,687 A | 9/1993 | Rybinski et al. ............ 426/582 |
| 5,321,132 A | 6/1994 | Billmers et al. ............... 536/48 |
| 5,378,491 A | 1/1995 | Stanley et al. ............... 426/661 |
| 5,380,543 A | 1/1995 | Barz et al. ................... 426/582 |
| 5,523,111 A | 6/1996 | Nickel et al. ................ 426/661 |
| 5,567,464 A | 10/1996 | Barz et al. ................... 426/582 |
| 5,629,090 A | 5/1997 | Eastman .................... 428/402.2 |
| 5,679,396 A | 10/1997 | Finnocchiaro .............. 426/582 |
| 5,681,598 A | 10/1997 | Kuraishi et al. ............... 426/36 |
| 5,703,226 A * | 12/1997 | Nickel et al. ................ 536/107 |
| 5,711,986 A | 1/1998 | Chiu et al. .................. 426/658 |
| 5,755,890 A | 5/1998 | Yuan ............................. 127/71 |
| 5,807,601 A | 9/1998 | Carpenter et al. ........... 426/578 |
| 5,866,180 A | 2/1999 | Budolfsen et al. ............. 426/42 |
| 5,882,713 A | 3/1999 | Eskins et al. ................ 426/578 |
| 5,904,949 A | 5/1999 | Reddy et al. ................ 426/603 |
| 5,925,398 A | 7/1999 | Rizvi et al. .................. 426/582 |
| 6,054,302 A * | 4/2000 | Shi et al. ....................... 435/95 |
| 6,060,107 A | 5/2000 | Reddy ......................... 426/603 |
| 6,086,926 A | 7/2000 | Bruce et al. .................... 426/36 |
| 6,093,424 A | 7/2000 | Han et al. ...................... 426/42 |
| 6,096,524 A | 8/2000 | Shi et al. ....................... 435/99 |
| 6,113,953 A | 9/2000 | McMahon et al. ............. 426/36 |
| 6,224,914 B1 | 5/2001 | Han et al. ...................... 426/36 |
| 6,228,419 B1 | 5/2001 | Yuan et al. .................. 426/661 |
| 6,258,390 B1 | 7/2001 | Budtz ........................... 426/36 |
| 6,270,814 B1 | 8/2001 | Han et al. ...................... 426/36 |
| 6,319,526 B1 | 11/2001 | Dahlstrom et al. ............ 426/36 |

OTHER PUBLICATIONS

Derradji-Serghat et al., Starke, 1999, vol. 51, No. 10, p. 362-368, abstract.*
Richardson, Journal of Food Science, Molecular Mobilities of Instant Starch Gels Determined by Oxygen-17 and Carbon-13 Nuclear Magnetic Resonance, vol. 53, No. 4, 1988, pp. 1175-1180.
Food Technology, The Interfacial Key to Emulsion Stability, Oct. 1988, pp. 172-186.
Giese, Food Technology, Developing Low-Fat Meat Products, Apr. 1992, pp. 100-108.
Food Technology, Membrane Separation Technology Offers Processors Unlimited Potential, Sep. 1990, pp. 108-113.
Food Technology, Oat-Bran-Based Ingredient Blend Replaces Fat in Ground Beef and Pork Sausage, Nov. 1991, pp. 60-66.
Taki, Food Technology, Functional Blend Produces Low-Fat Meat Products to Meet Consumer Expectations, Nov. 1991, pp. 70-74.
Kennedy, Food Technology, Structured Lipids: Fats of the Future, Nov. 1991, pp. 76-79.
Torres et al., Food Technology, Polydextrose . . . and its Applications in Foods, Jul. 1981, pp. 44-57.
Wurzburg, Converted Starches, Modified Starches: Properties and Uses, pp. 17-33.
Wurzburg, Modified Starches: Properties and Uses, pp. 244-252.
Nara, Starch 30, Study on Relative Crystallinity of Moist Potato Starch, Nr. 4, S. (1978), pp. 111-114.
Ghiasi et al., Cereal Chemistry, Effects of Flour Components and Dough Ingredients on Starch Gelatinization, 60 (1) :58-61.
Spies et al., Cereal Chemistry, Effects of Sugars on Starch Gelatinization, 59 (2) :128-131.
Mussulman et al., Corn Starch Electron Microscopy, Electron Microscopy of Unmodified and Acid-Modified Corn Starches, vol. 45, Mar. 1968, pp. 162-171.

(Continued)

*Primary Examiner*—Ruth A Davis
(74) *Attorney, Agent, or Firm*—Barnes & Thornburg LLP

(57) ABSTRACT

Disclosed herein is a method for harvesting amylose host material comprising enzymatically treating starch after the starch has been chemically modified to uniformly insert a steric hindrance substituent.

9 Claims, 3 Drawing Sheets

OTHER PUBLICATIONS

Sievert et al., American Association of Cereal Chemists, Inc., Enzyme-Resistant Starch .I. Characterization and Evaluation by Enzymatic, Thermoanalytical, and Microscopic Methods, 66 (4) : 342-347.

Whistler et al., Effect of Acid Hydrolysis on Amylose, Effect of Acid Hydrolysis on the Retrogradation of Amylose, vol. 25, Nov. 1948, pp. 418-424.

Savage et al., The American Association of Cereal Chemists, Effects of Certain Sugars and Sugar Alcohols on the Swelling of Cornstarch Granules, 55 (4) :447-454.

Russell et al., Journal of Cereal Science 9, Characterisation of Resistant Starch from Wheat and Maize, (1989), pp. 1-15.

Jane et al., Cereal Chemistry, Preparation and Properties of Small-Particle Corn Starch, 69 (3) :280-283.

Wong et al., Emulsions, vol. 9, pp. 393-412.

Jane et al., Carbohydrate Research, Structure Studies of Amylose-V Complexes and Retrogaded Amylose by Action of Alpha Amylases, and a New Method for Preparing Amylodextrins, 132 (1984) pp. 105-118.

Battista et al., Journal of Applied Polymer Science, Colloidal Macromolecular Phenomena, vol. II, (1967), pp. 481-498.

Organization of Starch Granules, 7. Penetration of Starch Granules by Chemical Reagents, pp. 227-228.

Fats and Fatty Oils, vol. 9, pp. 795-810.

Bouchard et al., J. Agric. Food Chem., High-Performance Liquid Chromatographic Monitoring of Carbohydrate Fractions in Partially Hydrolyzed Corn Starch, 1988, 36, pp. 1188-1192.

Larsson et al., Starch, Annealing of Starch at an Intermediate Water Content, 43 Nr 6, S. pp. 227-231.

Food Engineering, New Generation of Foods with Reduced Fat, Jan. 1990, pp. 23-24.

Battista et al., Industrial and Engineering Chemistry, Microcrystalline Cellulose, vol. 54, No. 9, Sep. 1962, pp. 20-29.

Heat Preservation and Processing, Food Science, pp. 199-201.

Willhoft, The Bakers Digest, Recent Developments on the Bread Staling Problem, Dec. 1973, pp. 14-20.

Erdi et al., Journal of Colloid and Interface Science, Rheological Characteristics of Polymeric Microcrystal-Gels, vol. 28, No. 1, Sep. 1968, pp. 37-46.

Shannon et al., Starch $2^{nd}$ Edition, Genetics and Physiology of Starch Development, Chapter III, pp. 25-59.

* cited by examiner

AMYLOSE AND AMYLOPECTIN DERIVATIVES

I claim the benefit under Title 35, United States Code, § 120 to U.S. Provisional Application No. 60/490,905, filed Jul. 30, 2003, entitled STABILIZED, MELTABLE, HOST AMYLOSE AND AMYLOPECTIN DERIVED MOLECULES FOR COMPLEXING HYDROPHOBIC COMPOUNDS AND THEIR USE IN THE MANUFACTURE OF CHEESE AND OTHER FOOD AND INDUSTRIAL PRODUCTS.

BACKGROUND OF THE INVENTION

1. Field of the Invention

The present invention relates to the production of hydrophilic host amylose molecules that manipulate, or form clathrates with, hydrophobic guest molecules, termed herein as "guest/host" chemistry. A product is produced that may be dried and then rehydrated to retain its meltable, thermoreversible host characteristic. This host molecule, which may be termed as a dextrin, dextrin gel, modified amylose, or modified food starch may be also be co-dried with pre-installed guests or co-dried with companion ingredients for combinations of functionalities.

The low flavor amylose/hydrophobic-guest complex compound, or clathrate, of the present invention is useful for a wide variety of applications that encompass emulsification or encapsulation. The complex is also integral to subsequent processes, such as the interruption of hydrophilic/hydrophobic forces in products, such as cheese, to alter the composition of those products. The resulting alterations may then include the introduction of additional fats, water, proteins, or other ingredients for nutritional or cost reduction purposes. The present invention, inter alia, enables the upgrading of overaged and substandard cheeses and can provide flavor enhancement thereto.

2. Description of Related Art

Industries are constantly struggling with methods of combining hydrophobic substances into hydrophilic environments. In the food industry, emulsions are important in a wide range of products from salad dressings to nutritional formulations in which specialty lipids are incorporated. Traditional emulsifiers tend to function by providing molecules that have both hydrophilic ends and hydrophobic ends. The result of this mechanism is to encourage the formation of agglomerates of like-groups to form tiny droplets of fat, for example, surrounded by hydrophobic ends of emulsifier molecules. These types of emulsifiers, such as lecithin or egg yolks, often impart certain undesirable properties, such as flavor or color. In many cases the amount of emulsifier needed contributes to undesirable secondary effects, such as elevated cholesterol levels or structure inhibiting effects.

Previous technologies for the formation of guest/host complexes or host/guest complexes have, for the most part, involved the use of cyclodextrins, which are produced by the special enzymatic action upon starch by enzymes, such as cyclodextrin-transglycosylase or glucoamylase. This results in a closed doughnut type molecular structure.

The basic building blocks of cyclodextrin are gluco-monomers, which resemble a hexagon. Each hexagon is formed by five carbon atoms, numbered one through five, and one oxygen atom. A sixth carbon atom is also part of each gluco-monomer, but does not participate as a hexagon ring member. The carbon atoms 2, 3, and 6 each hold a hydrogen atom and a hydroxyl group. The hydroxyl groups, which are dipolar and repel anything nonpolar, prefer to attract water. The hydrogen atoms and the carbon atoms form C—H groups. These groups prefer a nonpolar environment and dislike a polar environment, such as water. The six, seven, or eight hexagons, depending on type of cyclodextrin, form a ring enclosure or torus so that all the hydroxyl groups, 18, 21, or 24 in all, are on the outside of the ring band and all of the C—H groups are on the inside. This shields the opposing functions from canceling their conflicting Van Der Waals' forces.

The nonpolar compound resides as a guest molecule inside the torus of the cyclodextrin. Because only 18 to 24 hydroxyl groups can fit on the outside of the ring's mantle, the water solubility is severely depressed when a cyclodextrin clathrates with a nonpolar compound. Therefore, the whole complex is no longer water-soluble.

Channel diameter and volume dimensions are fixed for any given type of cyclodextrin, as is the number of hydrophilic hydroxyl groups on the outside of the mantle. In each case, this number is three times the number of gluco-monomers that form the torus. Attempts to increase the number of hydroxyl groups and the channel volume by trying to achieve the stacked torus configuration have not succeeded and, as a result, in most cases the size of the hydrophobic guest molecule is greater than the cyclodextrin molecule. Thus, once a nonpolar compound has formed a clathrate with a cyclodextrin, the overall water-solubility remains less than is useful for many applications.

Cyclodextrin patents describe in detail the mechanisms and technology for producing donut-shaped host molecules to be used in that branch of host/guest science. Stacks of the torus-like bands of cyclodextrin to form nanotubes with multiples of 18, 21, or 24 hydroxyl groups to increase water solubility would be desirable, but seem unattainable. Cyclodextrins, however, are restricted by their geometry to certain set and specific dimensions and therefore have limitations on the selection of the size of their guests.

U.S. Pat. No. 2,876,160 discloses a process physical phenomenon that involves the preparation of a high solids solution of various film-forming starch materials to physically encapsulate hydrophobic materials.

U.S. Pat. No. 3,557,091 Produced a non-gelling starch derivative having a lowered swelling temperature without substantial depolymerization by soaking with derivatizing agent at a preferred temperature of 40-60° F. in the presence of ferric sulfate and hydrogen peroxide.

U.S. Pat. No. 3,839,320 discloses a process of preparing a slurry of starch in water within the approximate range of about pH 7.5 to 10.5 in a standard etherification reaction which may or may not precede an acetylation process using magnesium oxide or magnesium hydroxide as a buffering agent to control the pH of the subsequent acetylation.

U.S. Pat. No. 3,974,034 discloses malto-dextrins having a D.E. not substantially above about 20, prepared by the enzymatic hydrolysis of oxidized starch. Syrups of the malto-dextrins are said to be capable of remaining haze-free for long periods of time at high solids concentrations. The malto-dextrins are prepared by first liquefying and oxidizing starch at elevated temperatures to provide an oxidized and liquefied starch substantially free of residual starch granules, and in a subsequent step, converting the oxidized and liquefied starch with a bacterial alpha-amylase enzyme preparation to achieve a malto-dextrin product having a D.E. not substantially above about 20.

U.S. Pat. No. 4,048,435 discloses the preparation of highly substituted granular starches by reacting the starch in an aqueous system with a reagent capable of producing an acetal cross-linkage; reacting the resultant acetal cross-linked starch with a mono-functional esterifying or etherifying reagent under aqueous alkaline conditions and removing the acetal cross-linkages by treating under acid conditions. The highly substituted starches are said to be particularly useful in operations, such as papermaking, wherein the cross-linkages can be removed and the starch readily dispersed during a relatively low pH starch cooking process.

U.S. Pat. No. 4,192,783 discloses remoistenable adhesive compositions for use on pre-gummed substrates comprising, in aqueous medium, a low viscosity starch-acrylamide graft copolymer.

U.S. Pat. No. 4,499,116 discloses an imitation cheese product, which is functionally equivalent to a caseinate-based imitation cheese product, that contains selected edible modified starches as replacements for up to 80% by weight of the caseinate present in the cheese product. Suitable starches include pre-gelatinized converted starches having a water fluidity (WF) of about 5-90 and an amylose content of at least about 15% to below 40% and selected derivatives and/or crosslinked products thereof. Suitable converted starches include fluidity starches prepared by acid- or enzyme-conversion or oxidized starches prepared by treatment with up to about 2% active chlorine. The starches may be pre-gelatinized by drum-drying and jet-cooking, or jet-cooking and spray drying.

U.S. Pat. No. 4,501,888 discloses a process for acetylating (esterifying) starches including dispersing the starch in an organic acid; contacting the starch with an organic acid anhydride; and reacting the components in the presence of a quaternary ammonium halide.

U.S. Pat. No. 4,510,166 discloses converted starches, which with water form gels having a neutral taste and preferably a creamy, smooth consistency, are said to be suitable as fat- and/or oil-replacements in various foodstuffs, especially high fat- and/or oil-containing foodstuffs such as ice cream and mayonnaise. The starches (e.g., tapioca, corn, or potato) have a DE of less than 5 and their aqueous dispersions have a hot flow viscosity of at least about 10 sec. at 10-50% solids, and they are capable of forming gels having a strength of at least about 25 g. within 24 hrs. and 4° C. at 10-50% solids. The preferred starches are tapioca dextrins having a DE of about 2 or less and hot flow viscosity and gel strength of about 20-100 sec. and 65-930 g. at 25-35% solids. Acid- and enzyme-converted starches are also said to be suitable.

U.S. Pat. Nos. 4,608,265 and 4,695,475 disclose an imitation cheese product which is functionally equivalent to a caseinate-based imitation cheese product, contains pre-gelatinized modified high amylose starches, preferably converted and/or derivatized, as partial or total replacement for the caseinate present in the cheese. Suitable converted starches include fluidity starches prepared by acid- or enzyme-conversion, oxidized starch prepared by treatment with less than 5% active chlorine, and dextrins having a calcium chloride water fluidity of less than about 50. Suitable derivatives are prepared by treatment with up to 25% propylene oxide, 5% succinic anhydride, and 10% octenylsuccinic anhydride or with a sufficient amount of acetic anhydride or sodium or potassium ortho or tripolyphosphate to provide a maximum of 6% bound acetyl or 0.8% bound phosphate. Mixtures of modified or unmodified high amylose starches with up to 80% by weight of other starches (0-40% amylose) are also suitable. In a preferred embodiment, the cheese is an imitation mozzarella cheese said to be substantially equivalent to the caseinate-based imitation cheese in all properties.

U.S. Pat. No. 4,840,807 discloses branched dextrin and linear oligosaccharides that are produced by degrading starch with alpha-amylase followed by fractionating with a gel-type filtering agent. The branched dextrin is said to be useful in the food fabrication.

U.S. Pat. No. 4,937,091 discloses the replacement in whole, or in part, of caseinates which provide imitation cheeses with desirable texture, melt and oil emulsification characteristics by pregelatinized debranched starches which have been enzymatically prepared by hydrolyzing all, or part, of the alpha-1,6-D-glycosidic bonds of branched starch molecules (amylpectin). The debranched starches may be derivatized, converted or crosslinked, or blended with other selected starches in imitation cheeses.

U.S. Pat. No. 4,971,723 discloses partially debranched starch, prepared by enzymatic hydrolysis of the alpha-1,6-D-glucosidic bonds of the starch, comprising amylopectin, partially debranched amylopectin and up to 80%, by weight, short chain amylose. A method for preparing this starch, employing an endo-alpha-1,6-D-glucanohydrolase is also disclosed. The starch is said to be useful for lending a fat-like, lubricating texture to aqueous dispersions, forming stable opaque clouds, forming thermoreversible gels, high strength gels and water-resistant films, and for thickening and bonding.

U.S. Pat. Nos. 4,977,252 and 5,185,176 disclose the preparation of modified starches said to be useful for emulsifying industrial products, especially foods and beverages containing flavor oils, by enzymatic degradation of the 1,4-alpha-D-glucosidic linkages from the non-reducing ends of a starch molecule, preferably employing beta-amylase, which may be carried out before or after the preparation of a starch derivative containing a hydrophobic group or both hydrophilic and hydrophobic substituent groups. The enzymatic degradation provides a starch emulsifier whose emulsions are said to be characterized by improved shelf stability, which emulsifier may be used as a replacement for gum arabic and in other industrial applications.

U.S. Pat. No. 5,164,215 discloses a batter starch that is esterified to have a degree of substitution between 0.02 to 0.1, and a protein content greater than or equal to 1.0%. The starch is obtained from a starch bearing plant of the duh homozygous genotype. Maize is the preferred source for the starch and the preferred protein source is gluten. The preferred esterification agent is acetic anhydride.

U.S. Pat. No. 5,200,216 discloses that in the manufacture of mozzarella cheese, aging can be dispensed with if the process is controlled to yield a combined moisture and wet milkfat content of at least about 70 weight percent, and the cheese will provide acceptable bake performance under typical cooking conditions used in the pizza industry today. Within about 48 hours after brining, the cheese should either be used or frozen. In a continuous process, the hot stretched cheese from the kneading machine is extruded directly into cold brine. After the cheese has cooled sufficiently, it can be comminuted and frozen by independent quick freezing, preferably in a fluidized bed freezer. Salt preferably is mixed into the cheese during the kneading step.

U.S. Pat. No. 5,244,687 discloses a no-fat cheese analog having the texture, body and eating qualities of cheese is produced by admixing about 15% to about 35% of a coagulated skim milk product having a fat content of less than 2%, about 15% to about 35% dry particulate rennet casein, about 1% to about 3% of an edible emulsifying salt, sufficient quantities of flavoring agents and acidulants to impart desired flavor and pH, and about 30% to about 65% water; the dry rennet casein being hydrated in the water by action of the emulsifying salt at temperatures of about 160° F. to about 200° F. under agitation conditions for a time period sufficient to provide a plastic homogenous body being substantially free of unhydrated rennet casein particles, the edible emulsifying salt being present at about 2% to about 15% by weight of the said particulate rennet casein, the emulsifying salt being selected from the group consisting of alkali metal phosphates, citrate salts and mixtures thereof.

U.S. Pat. No. 5,321,132 discloses the preparation of starch esters having an intermediate DS of about 0.5 to 1.8 in an aqueous one step process by reacting starch with high treatment levels of organic acid anhydride and high concentrations of alkaline reagent.

U.S. Pat. No. 5,378,491 discloses a method for preparing reduced fat foods which employs a fragmented, granular amylose starch having a melting onset temperature (as measured by differential scanning calorimetry) of greater than about 70° C. when measured at 20% starch hydrolysate solids. The fragmented, granular amylose starch hydrolysate is prepared by hydrolyzing a granular amylose starch in a strongly acidic aqueous slurry at a temperature greater than 70° C. or by hydrolysis at a lower temperature followed by heating a slurry, after neutralization, to raise the melting onset temperature. Also disclosed are food formulations in which the fragmented, granular amylose starch hydrolysate is used to replace fat and aqueous dispersions of the fragmented, granular amylose starch hydrolysate which are useful therein.

U.S. Pat. No. 5,380,543 discloses that by adding a minor amount of starch to a natural mozzarella cheese, the baking characteristics of the cheese when used to make a pizza can be altered, making it more suitable for a particular set of baking conditions, e.g., involving time, temperature, type of oven, crust thickness, and the toppings used. For example, the addition of about 0.001 to 0.01 wt. % of a modified high amylose starch allows a pizza with a partially pre-baked crust to be baked at 685° F. in an impingement oven in as little time as 70 seconds, with the cheese being fully melted, evenly browned, and covered with small blisters, as is desired, and the crust being properly baked. Without the addition of the starch, the cheese, although melted, is not brown or blistered by the time the crust is "done."

U.S. Pat. No. 5,523,111 discloses a process for the formation of clathrate inclusion complexes comprising suspending a suitable starting material such as acetylated starch in water, heating the resulting suspension past the gelation point of the starting material, cooling the resulting hydrocolloid to just above the convolution temperature of the starting material, cooling the resulting hydrogel while adding a lipid such as a triglyceride and homogenizing the resulting product at a temperature below the melting point of the lipid in the case of fats and 45° C. in the case of oils.

U.S. Pat. No. 5,567,464 discloses a process of manufacturing a mozzarella (or mozzarella-like) cheese comprising the steps of a) pasteurizing cow's milk; b) acidifying the milk to convert it to a cheese milk; c) coagulating the cheese milk to obtain a coagulum comprised of curd and whey; d) cutting the coagulum and draining the whey therefrom, thereby leaving a cheese curd; e) heating, kneading, and stretching the cheese curd until it is a homogeneous, fibrous mass of heated, unripened cheese; f) forming the heated cheese into a shape; g) cooling the shaped cheese in cold brine; and h) removing the cooled cheese from the brine. The process is improved by mixing an emulsifier such as a sodium phosphate or citrate into the heated cheese after it has been heated, kneaded, and stretched, but before it has been formed into a shape. It is said that the resultant cheese provides good baking performance over a wider range of conditions than the equivalent cheese without emulsifier, and that it is particularly useful as the stuffing cheese for stuffed crust pizza or as the exposed topping cheese on pizzas.

U.S. Pat. No. 5,629,090 discloses a starch hydrolysate composition that is said to be particularly suited for use as a sequesterer, i.e., it readily interacts noncovalently with other molecules to form stable inclusion complexes which are useful in a variety of applications. The starch molecules in the composition which act as sequesterers are in the form of single helical inclusion complexes with starch molecules having a D.P. of about 10 to 200 and a weight-average D.P. of about 10 to 50 as the host molecule holding one or more guest molecules within their internal cavities. These hydrolysates are prepared by first converting amylopectin molecules from the double helix form to the single helix form and then by cleaving chain segments from the molecules.

U.S. Pat. No. 5,679,396 discloses fat free, reduced fat and low fat cheeses, including natural cheese and processed cheese, and method for making the cheeses. The natural cheeses and processed cheeses contain a pre-gelatinized, high amylose starch based texturizing agent that can partially or totally replace fat and/or fillers which are traditionally incorporated into cheese formulations. The natural cheeses and processed cheeses are said to have the textural and organoleptic mouthfeel properties of full fat, conventional natural cheeses and processed cheeses.

U.S. Pat. No. 5,681,598 discloses a process for producing natural cheese, characterized in that a transglutaminase is included therein for a reaction. The process can provide a large amount of cheese curd compared to conventional methods, making it possible to efficiently use the starting milk. Further, the obtained cheese is said to have an excellent flavor, texture and appearance.

U.S. Pat. No. 5,703,226 discloses a process for the uniform acylation of starch comprising preconditioning the starch with a base for at least six hours, adjusting the pH to a suitable range for acylation, adding the desired acylation agent and isolating the acylated starch. A continuous method for acylating starch is also described.

U.S. Pat. No. 5,711,986 discloses a fat-like carbohydrate, containing 12 to 100%, by weight, short chain amylose, wherein the fat-like carbohydrate is used in foods in an amount effective to function as a replacement for up to 100%, by weight, of one or more fat(s) contained in foods. The short chain amylose may be prepared by the enzymatic debranching of starch, employing an enzyme which specifically degrades the alpha-1,6-D-glucosidic-linkages of the starch molecule. A method of replacing up to 100% of one or more fat(s) contained in foods, wherein the food containing the enzymatically debranched starch exhibits functional and organoleptic qualities equivalent to those of the food containing conventional amounts of fat. Also provided are foods containing the short chain amylose materials in place of fat, cream, oil, oil-in-water and water-in-oil emulsions and other lipids which are conventional components of the foods. These foods include: ice cream, spoonable and pourable salad dressings, margarine, low-fat spreads, low-fat cheeses, baked goods, breaded foods, sauces, whipped toppings, icings, puddings and custards, mayonnaise and coffee whiteners.

U.S. Pat. No. 5,755,890 discloses a method of producing starch-emulsifier compositions by heating a starch in the presence of an emulsifier to form a complex. The product can be further treated to obtain greater than about 20% short chain amylose. Starch-emulsifier compositions (e.g., powders, gels, pastes) produced by this method and food products containing the starch-emulsifier composition are also described.

U.S. Pat. No. 5,807,601 discloses an imitation cheese composition that is made with less than 2% protein and/or less than 1% casein protein and comprises a) about 3% to about 30% starch; b) about 0% to about 30% edible lipid material; c) about 20% to about 60% water; d) about 0.5% to about 25% non-starch carbohydrates; and e) about 0.5% to about 5% hydrocolloid stabilizers; and optionally contains up to about 2% cheese flavor and up to about 2% color.

U.S. Pat. No. 5,866,180 discloses a method for production of an acidified edible gel on milk basis that comprises addition of transglutaminase to milk, followed by a heat treatment. A functionally and/or organoleptically satisfactory edible gel is obtained, which can be used as a yoghurt mousse or cheese.

U.S. Pat. No. 5,882,713 discloses a stable and non-separable composition comprised of starch and a water-immiscible material that can be prepared in the absence of external emulsifying or dispersing agents by thoroughly solubilizing an aqueous dispersion of the starch at elevated temperatures and incorporating the water-immiscible material into the non-retrograded starch under conditions of high turbulence. The resulting dispersions form soft gels that can be converted to pourable fluids by the application of heat. Upon drying, these dispersions yield solid compositions that can be redispersed in water to form smooth, stable dispersions. These compositions are said to be useful as thickening agents, suspending agents, waterproof coating materials, adhesives, fat substitutes, and seed coatings. They are receptive to the addition of a variety of other water-immiscible materials, such as volatile and essential oils, food flavorants, medicinals, waxes, agricultural chemicals, and the like.

U.S. Pat. No. 5,904,949 discloses a fat continuous spread having up to about 65 wt % fat and a dispersed aqueous phase which contains an amylose containing gelling starch characterized by a $G'_{eq}$ of 400 dyne/cm$^2$ or greater and a critical strain value ($\gamma$cr) of 12 or greater at 10° C. provided the starch is prepared at a concentration having an anhydrous starch solid content of 10 wt %.

U.S. Pat. No. 5,925,398 discloses a method of making processed mozzarella cheese that does not require any aging or refrigeration during storage. This is accomplished by dicing cheese curd, adding emulsifier, and thermomechanically treating in an extruder to stretch and cook the curd. Fresh processed mozzarella cheese having functionality similar to the aged mozzarella cheese is achieved by addition of emulsifier to soften casein and inputting sufficient mechanical energy to establish the appropriate fibrous structure. Longer shelf-life and storage without refrigeration is achieved by application of suitable time-temperature combination to inactivate proteolytic enzymes and microorganisms.

U.S. Pat. No. 6,060,107 discloses a multi functional edible spread having both a fat and aqueous phase. The spread contains 65 wt % or less triglyceride fat and 0.5 wt % to 12 wt % emulsifiers. At least a portion of the emulsifiers are incorporated into the aqueous phase and are complexed in a starch based clathrate to diminish the taste and flavor problems associated with emulsifiers.

U.S. Pat. No. 6,086,926 discloses pasta filata cheeses, such as mozzarella, that are made in the conventional way, except that the conventional step of heating and stretching is replaced by treatment with a proteolytic enzyme, thereby providing for significant economies in manufacture. Brine treatment may also be replaced by dry salting in this method.

U.S. Pat. No. 6,093,424 discloses a cheese curd that contains protein products originating from a dairy liquid containing casein and whey protein. In order to obtain the cheese curd, the dairy liquid is acted upon by a transglutaminase and a non-rennet protease, resulting in a substantial proportion of whey protein products being retained in the cheese curd. The invention also discloses a method of making the cheese curd that retains a substantial proportion of whey protein products. Also disclosed are cheese product, such as a soft cheese, a semi-soft cheese, or a hard cheese, that contains protein products originating from a dairy liquid containing casein and whey protein, and a method of making the cheese product.

U.S. Pat. No. 6,113,953 discloses a fat-free or lower-fat pizza cheese said to have excellent melt properties for baking on a pizza without the need for aging and a method of making thereof. The process of manufacturing such fat-free or low-fat mozzarella cheese comprises mixing a food grade acid with liquid milk having a fat content less than 1.5% or a casein to fat weight ratio of greater than 1.5. The acidified milk is then coagulated and processed into pizza cheese. No aging is necessary to obtain excellent melting properties. In a preferred embodiment, after coagulation of the milk and cutting of the curd, a portion of the whey is drained and glucono-δ-lactone is added to gradually further decrease the pH. The remaining whey is then drained and the resulting curd is processed into mozzarella cheese. A method of making a fat-free or low-fat process pizza cheese is also disclosed.

U.S. Pat. No. 6,224,914 discloses a cheese curd containing a substantial proportion of whey protein products and curded proteins originating from a dairy liquid containing casein, as well as a process for making the cheese curd. The process includes the step that a dairy liquid fortified with whey protein is contacted with a transglutaminase to provide a modified dairy liquid containing whey protein products. The modified dairy liquid is then blended with a second dairy liquid and rennetted to provide the curd, whereby a high proportion of whey protein products is retained in the curd. The curd can be used to prepare cheese products, including soft, semi-soft, and hard cheeses, where the cheese products contain a substantial proportion of whey protein products and curded proteins originating from dairy liquids.

U.S. Pat. No. 6,228,419 discloses a method of producing high-amylose based starch-emulsifier compositions by heating a high-amylose starch in the presence of an emulsifier to form a complex with unique properties. High-amylose starch-emulsifier compositions (e.g., powders, gels, pastes) produced by this method and food products containing the high-amylose starch-emulsifier composition are also described.

U.S. Pat. No. 6,258,390 discloses a process for making cheese including: a) adding to cheesemilk a transglutaminase, incubating for a suitable period, b) incubating with a rennet so as to cause clotting, and c) separating whey from the coagulate, and d) processing the coagulate into cheese. Cheese products produced by the process are contemplated as is the use of transglutaminase for maintaining proteins in the cheese material during a conventional cheese-making process.

U.S. Pat. No. 6,270,814 discloses a process cheese product made with a cheese and dairy liquid that includes casein, whey protein, and lactose, wherein at least a portion of the casein and/or whey protein in the dairy liquid is crosslinked via γ-carboxyl-ϵ-amino crosslinks prior to being combined with the cheese, and wherein the lactose in the process cheese product remains dissolved in the aqueous phase upon storage. This product is provided by a process that includes the step of contacting the dairy liquid with a transglutaminase for a time, and under conditions, sufficient to crosslink at least a portion of the casein and/or whey protein to provide crosslinked protein conjugates in the dairy liquid. A process for making the process cheese product is also disclosed. Advantageously, the process permits replacing part of the cheese proteins with the crosslinked proteins of the dairy liquid. Additionally, crystallization of lactose in the process cheese product is inhibited such that lactose levels higher than commonly introduced in cheese products may be employed in the process cheese.

U.S. Pat. No. 6,319,526 discloses a process of manufacturing a mozzarella variety of cheese or a mozzarella-like cheese wherein a milk composition is pasteurized and formed into a coagulum. The coagulum is cut to separate curd from whey and the whey is drained therefrom. The curd is then heated preferably in a liquid-free environment and mechanically worked until the curd forms a fibrous mass. The cheese is then formed into a selected shape. Additionally, generally recognized as safe (GRAS) ingredients are added after the whey is drained but prior to heating the curd. In addition, the curd may be comminuted to a selected size after the whey is drained.

The literature describes numerous starch patents and technologies involving a myriad of methods to chemically and enzymatically modify starch materials to change their characteristics and to degrade their structures or to trap non-starch components. Some of the known art involves treatment of starch at high pH levels, for example, as is known in the various cross-linking technologies. Other art describes various methods for producing starch derivatives.

Further insight regarding the manipulation of hydroxyl groups on glucomonomers may be gained from a study of cellulose chemistry and, while starch components cannot be subjected to the extremes of cellulose processing, certain principles apply. Warwicker "Celluloses and Its Derivatives", discusses the structure and morphology of cellulose and the postulated factors influencing the engineering of cellulose from a variety of sources. Warwicker states that while cellulose is similar to starch in that they are constructed of glucomonomers and although the beta 1-4 linkages between glucomonomers in cellulose are much more tenacious than the alpha 1-4 and alpha 1-6 linkages in starch nevertheless a study of this field gives some valuable insight into more precise engineering of starch molecules particularly the various amyloses.

The disclosures of the foregoing are incorporated herein by reference in their entirety.

SUMMARY OF THE INVENTION

The present invention relates to a method of combining hydrophobic materials into hydrophilic environments with virtually no flavor contribution and with a very flexible degree of structural engineering.

The method involves the formation of clathrates to combine oils and water. Clathrates are the formation of complexes in which one molecule is encapsulated inside another host molecule. Some definitions require that encapsulation be via a caged structure, that is to say, a structure from which the guest molecule cannot escape. Other definitions include any type of non-ionic control of guest materials. By this definition, clathrate technology is based on guest/host chemistry where one molecule includes or occludes another molecule, similar to molecular encapsulation, but the molecules are not locked away or imprisoned. Guest/host technology encourages the formation of water-soluble helical complexes, or inclusion complexes, of compounds such as fatty acids that are not in themselves water-soluble.

The present invention involves the creation of dynamic host molecules resembling nanotubes that are restricted from retrogradation, thereby permitting permanent reversibility in which the newly meltable host molecule is able to accept guests at any appropriate temperature and any number of times by a process comprising:

1. placing substituents evenly spaced along the amylose and amylette chains to serve two purposes; to prevent the helices from recoiling completely (retrograding), and protecting the 1-4 linkages of the helices from excessive enzymatic cleavage;
2. cooking the starch completely to hydrate the molecule;
3. cooling the cooked starch gel to a suitable temperature for alpha amylase introduction; and
4. inactivating the enzyme to achieve the desired and predictable end product characteristic.

More particularly, the present invention is directed to a method for harvesting amylose host material comprising enzymatically treating starch after the starch has been chemically modified to uniformly insert a steric hindrance substituent.

In a preferred embodiment, the present invention is directed to a method of producing stabilized, meltable, hydrophilic, starch derived amylose and amylopectin host molecules capable of forming guest/host complexes with hydrophobic compounds comprising the steps of:

(A) slurrying starch in water in the presence of a base;
(B) cooling the slurry to a temperature below ambient;
(C) at least partially esterifying the starch by adding an esterifying agent at a pH above neutral and a temperature below ambient;
(D) allowing the pH to drop below neutral;
(E) diluting and washing the starch slurry;
(F) hydrating the washed starch by heating;
(G) dissolving the hydrated starch in water and heating;
(H) cooling the starch to a temperature suitable for alpha amylase introduction;
(I) adding alpha amylase and holding until a pre-determined desired viscosity is attained; and
(J) heating to 92° C. to 105° C. to inactivate the enzyme.

In a further embodiment, the present invention is directed to a method of managing protein/lipid complexes in cheese by incorporating a host molecule into cheese after curd formation but prior to cooking or stretching wherein said host molecule is an amylose host molecule prepared by enzymatically treating starch after the starch has been chemically modified to uniformly insert a steric hindrance substituent.

DESCRIPTION OF THE PREFERRED EMBODIMENTS

Figure 1:
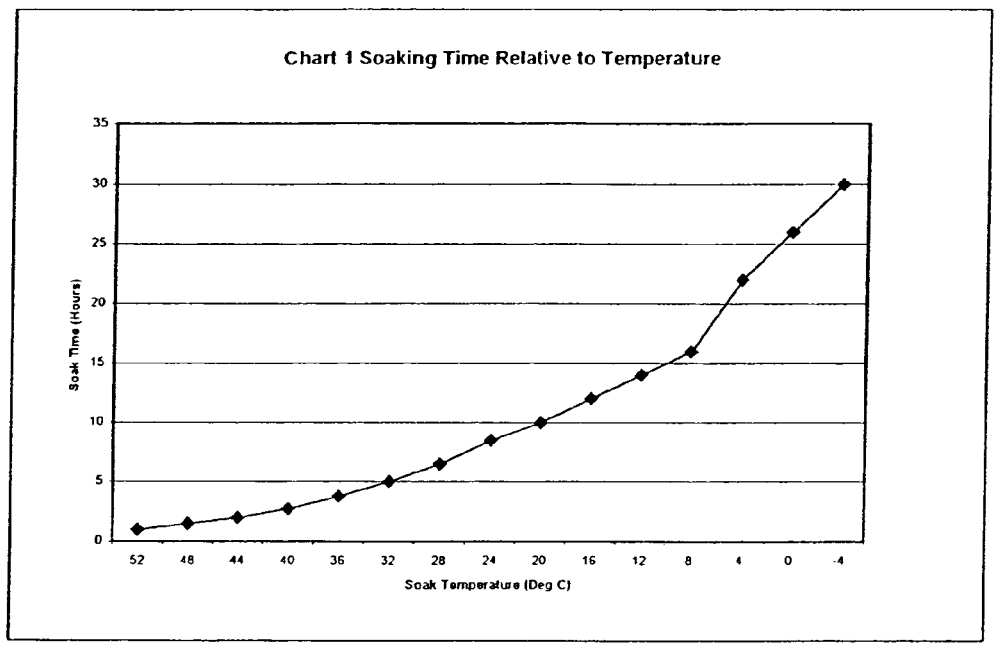
FIG. 1 is a graph showing the effect of pretreatment time and temperature at pH 10 on medium amylose starches.
Figure 2:
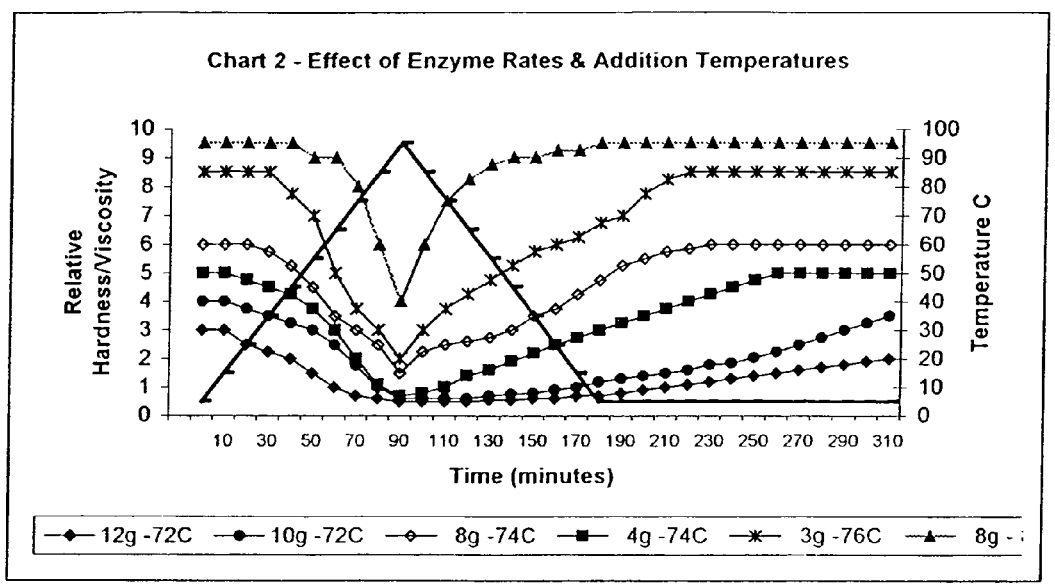
FIG. 2 is a graph showing the impact of varying the enzyme addition amount and the temperature at which the enzyme is added during a fixed reheating process. The graph represents the relative viscosity or, in the case of a formed, cooled hydrogel, the hardness of the products of this invention at various temperatures. The data points represent individual samples measured after they have been cycled to point of evaluation. The data points are expressed in grams of enzyme per 250-gallon batch of a 20% solids modified starch solution and the temperature at which the enzyme was added in a constant energy reheating reactor.
Figure 3:
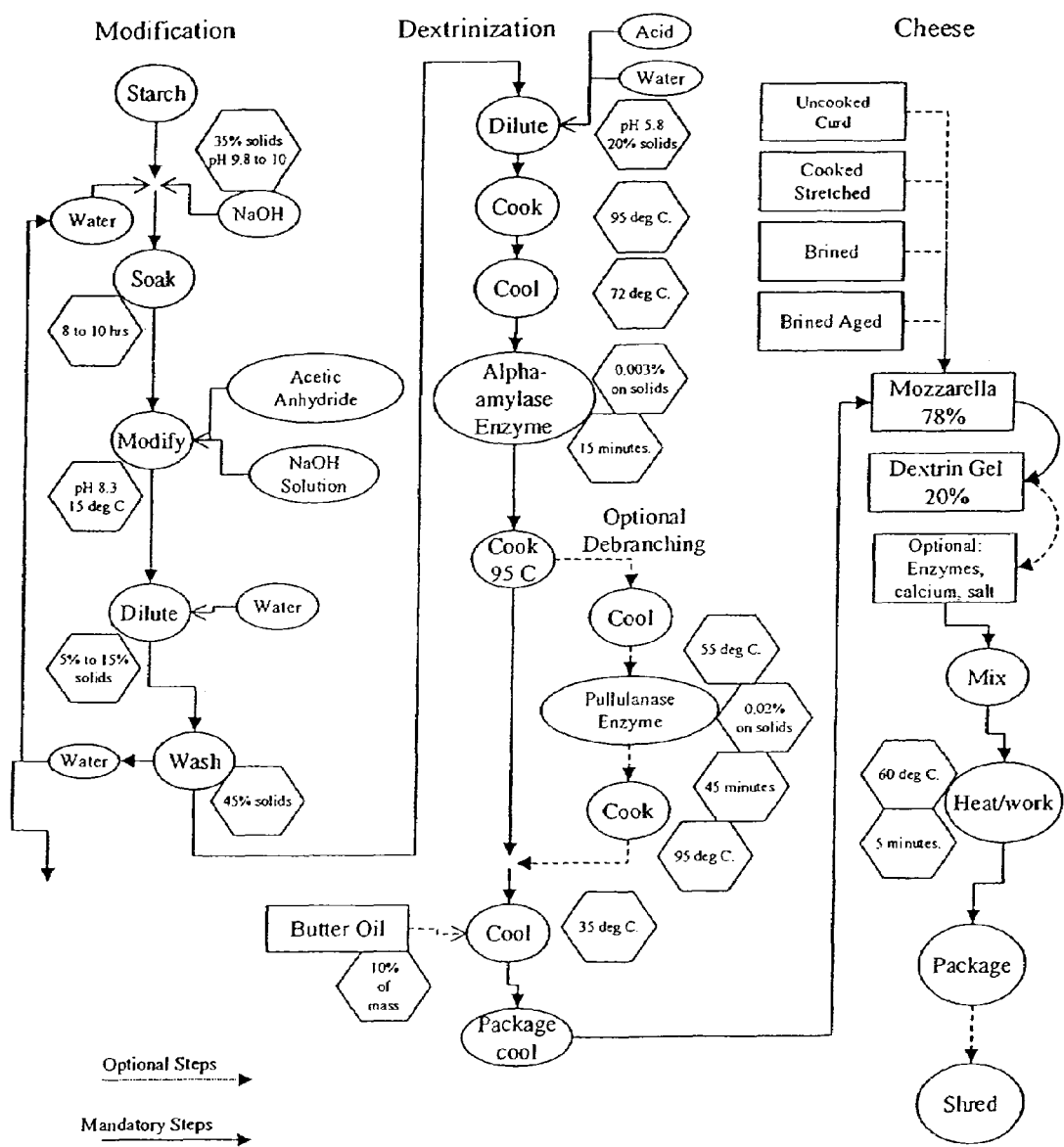
FIG. 3 is a schematic diagram of the overall cheese manufacturing process of the present invention.

While naturally formed amylose lipid complexes are well known, they are severely restricted in their ability to control those lipids through storage. First, the amylose molecule in its natural state is generally very prone to retrogradation, which limits the amount of fat which may the complexed and held, whereas the present invention provides stabilized amylose that has fat holding capability in excess of 10 times that of natural amylose. Further, natural amylose produces gels that are generally not reversible whereas the present invention produces thermo reversible or meltable gels. Still further, the present invention enables the engineering of those host amylose type molecules with selectable melt points, viscosity, and re-solidification profiles.

The technology of the present invention allows a practitioner to engineer and define the size and geometry of the host molecules to manage a wide range of hydrophobic guests. This technology has the further advantage that the molecule is produced using substances and variations of traditional processes that are Generally Recognized As Safe (GRAS) in an entirely food grade process.

Accordingly, a stabilized host molecule can be obtained by engineering the configuration of amylose molecules obtained from starch, whereby
a) the finished host molecule has CH groups facing inside to a hydrophobic core of a stabilized, helical, molecular, amylose tube;
b) the water-soluble host molecule is water-soluble because hydroxyl groups face the outside on the hydrophilic outer mantel of the tube.

When exposed to a dissolved host molecule, the fatty acid legs of lipids are attracted, as guests, to the hydrophobic or lipophilic core of the molecule. Therefore, this mechanism can be used to create molecular dispersions of lipids and certain other hydrophobic materials in water.

These molecular dispersions, which differ from emulsions, can offer new dimensions in fat management including magnifying the impact of oil based flavors, increasing the exposure of lipids to enzymatic action, stabilizing emulsions, extending mouthfeel of fats, and reducing fat requirements.

A secondary effect of the chemistry is to create an emulsifier produced in situ. The dynamic amylose/lipid complex itself becomes a good emulsification agent and this ability, by itself, offers many applications. In its simplest form, the material acts as a host to one leg of a triglyceride leaving the glycerol and two fatty acid legs exposed. This can be expressed as a stoichiometric ratio in which a specific number of moles of host molecules represent the ability to harbor an equivalent number of moles of potential hydrophobic guests under ideal conditions. As the available core cavities are filled, the newly formed guest/host molecule complexes are characterized as complexes of water-soluble outer mantels with oil soluble triglyceride guest fragments sticking out of one end. In essence the complex takes on the classical definition of an emulsifier. This complexed structure begins to resemble an emulsifier and attractions of other fat molecules begin to give an emulsified structural appearance as fat globules build on the complexed triglyceride. This provides a secondary emulsifying capacity as the complex begins to act more as a traditional emulsifier.

The host molecule has an additional attribute. The amylose chain is an excellent film former and as foods containing a guest/host molecule are chewed, the complex is temporarily held on the palate as a film containing hydrophobic flavor components. As saliva enzymes degrade the film, the flavor components are sequentially released enhancing and prolonging flavor perception.

Additionally, the remaining available hydroxyl groups of outer mantel of the guest/host complex act as a sponges carrying bound, secondary, and tertiary water into the food system. This water, which has varying degrees of availability, provides an ability for selective hydration of native components, such as proteins, thus allowing an additional dimension of engineering for the overall product.

Amylose tends to form an alpha helix with seven glucomonomers per turn and then the number of hydrophilic groups is three times the degree of polymerizations. However, with non-modified amylose, the benefit of this large product is unavailable because the energy barrier is larger to hydrate the hydrogen bridge bonds, which locks up the large molecule, and the tendency to return to this state is equally strong. Amylose, as such, will take advantage of the two possibilities to undergo hexagonally closest (HCP) or face-centered cubic packing (FCCP).

Typically, modification of amylose and amylopectin tends to be concentrated in the amorphous regions of the C type legume starches, while the molecules in the crystalline regions receive less esterification. As a result, unmodified amylose from the center of the granule can exert an undue influence on the over-modified surface molecules so that when the unmodified amylose retrogrades in its natural fashion it overpowers the modified material effectively negating the visible effects of the system. It is important to begin with substantially purified starch because starch-containing-substrates, such as pea flour, have too many conflicting components, such as non-starch polysaccharides and proteins, that prevent the production of the predictable modification of the amylose and amylopectin fractions. Such predictability is essential for subsequent engineering of chain length.

In modified amylose, the energy barrier to hydrate the remaining skeleton is lowered, as is the tendency to retrograde and undergo closest packing, either HCP or FCCP. In addition, there is control over the dissociation constants of such a complex via the degree of polymerization, which is chosen by hydrolysis. Thus, many combinations are possible, giving good control over the magnitude of dispersion, viscosity, and dissociation constants.

In polar environments, hydrophobic fatty materials would prefer to harbor themselves in the hydrophobic core of the helix, but proximity is a key factor since ionic attraction is not a factor in the attraction of the guests. The guests must stumble across these oil-friendly zones and so time, temperature, physical mixing, and shear play a role in the degree of population of available host zones. Also, the degree of polymerization of the host influences the availability of host cavities. Longer chains of modified amylose close in on themselves more completely and only the kinks in the chains are visible or available for hosting. Amylose with a high degree of polymerization has a greater tendency to form rigid gels on cooling and this restricts the temperatures at which complexing can take place. Uniform hydrolysis of the chains can inhibit this gelling tendency and make the helical cavities more available to hydrophobic guests over a longer period of time and at a lower temperature.

Acid hydrolysis is a very crude method of shortening the amylose chains. It is very temperature dependant and somewhat uncontrollable resulting in mixtures of varying chain lengths. Low pH environments also result in the dismantling or removal of the substituent acetyl groups thus removing the amylose stabilizing components. Without a predictable substituent construction the resulting gels will release gust material in a haphazard fashion. The use of a suitable enzyme, when combined with specific temperature thresholds to cleave bonds selectively, preserves these substituents, thereby resulting in a product of much more predictable uniformity and effectiveness. The host molecule can thus be engineered in this fashion to yield a material that can act as a host to hydrophobic materials at a much wider range of temperatures and concentrations and can be dried while retaining its hosting/emulsification capabilities.

The foundation of the guest/host technology of the present invention is the uniform chemical and enzymatic modification of amylose and amylopectin derived from starch. The raw material may be any starch such as, but not limited to, pea, corn, potato, rice, wheat, tapioca, or any starch having an amylose content or having a content of amylopectin containing amylose-like ends. Higher degrees of polymerization of the amylose fraction offer an additional flexibility of functionality of subsequent products. Legume starches, particularly pea, mung bean, adzuki bean, and lentil starches are more desirable because they have a C type crystallinity and the A-chains of the amylopectin molecules can be liberated or harvested with a higher yield to serve as short chain amylose type hosts.

Individual starch molecules within the starch granule are found both as amylose, slightly-branched chains comprised mostly of $\alpha$-1,4-linkages between the anhydroglucose units, and amylopectin, highly-branched chains consisting of both $\alpha$-1,4- and $\alpha$-1,6-linkages. See Whistler, R., et al. (eds.), *Starch: Chemistry and Technology*, 2d ed., Academic Press, Inc., 1984, pp. 154-155 and 260.

The amylopectin molecule contains three types of chains: C-chains, B-chains, and A-chains. Manners, D., "*Recent Developments in Our Understanding of Amylopectin Structure*," *Carbohydrate Polymers*, Vol. 11, 1989, pp. 87-112. The amylopectin molecule has only one reducing group and it is located on the root C-chain. Numerous B-chains are attached to the C-chain structure and are bound to two or more chains. In typical starches, A-chains contain about 12 to 16 anhydroglucose units. These A-chains are also distinctive in that they are attached in individual clusters to the B-Chains and, reminiscent of end branches on a willow tree, are a main source of amylose-type molecule fragments. That is to say, when these A-chains are separated from their B-chain roots, they are comprised only of $\alpha$-1,4 linkages. The characteristic 1,6 linkages of amylopectin remain with the B-chain and C-chain components of the original structure.

Some native starch is in the form of a double helix. Some of the amylose ends of the A-chain amylose attached to the amylopectin structure are more likely in this parallel or winding chain structure, while the amylose molecules themselves are more likely single helixes. Galliard, T., *Starch: Properties and Potential*, John Wiley & Sons, 1987, pp. 69-75.

It has been reported that pea starches, like other members of the Legumiosae family, have A-chain lengths that are longer than those of dent corn, for example. Rather than 12-16 anhydroglucose units per branch, pea starches have been shown to have 20-24 anhydroglucose units per A-chain. Pea starch and other members of the Legumiosae family also show a different type of crystallinity from cereal or root derived starches. Under x-ray radiation cereal starches are characterized by the A pattern of crystallinity while root starches the B type. Pea starches exhibit a third C type crystallinity, which is a form of a combination of the first two, typical in part, of both A and B.

Furthermore, the starch granules of some varieties, such as legume starches, are formed in alternating crystalline and amorphous regions or layers, so it is necessary to pretreat the starch with an agent to prepare the granule for penetration by the acetylating agent.

The appropriate modification should yield molecules within a starch granule that is uniformly modified rather than surface modified. Esterification with any of the esterification agents known to the art is suitable. Starch esters of this type include, but are not limited to, starch acetate, starch propionate, starch butyrate, starch hexanoate using acetic anhydride, propionic anhydride, butyrate anhydride, hexanoate anhydride, and the like. Esterification with acetic anhydride is preferred. The modification may be conducted on soaked granules or on pre-gelatinized hydrolyzed gels. The advantage of the granular modification is the ease of removing sodium acetate byproducts. The advantage of pre-gelled material is that the molecule can be sized for specific application and the resulting modification is more predictable and uniform. Because the typical usage of this material in a food is low, the byproducts normally do not conflict with the intended food application.

The acetylation modification stabilizes the amylose molecule in a helical configuration. The amylose in unmodified starch retrogrades after it has been heated and then cooled. At high temperatures, the molecule stretches out and, as it cools, becomes a tight coil. In between these two points, the amylose molecule is a helix. The target esterification modification stabilizes the amylose molecule at this point by placing a substituent every seventh gluco-monomer; there being seven gluco-monomers per turn. These derivatized gluco-monomers prevent the amylose from shrinking and recoiling after cooking. The resulting helix is not rigid; it can flex and bend. The helix creates a super dispersion by scintillating molecules of fat. The rate is determined by the configuration and molecular shape of the molecule and the ambient temperature.

When this helix comes in contact with a fat globule, some of the individual fat molecules are attracted to the lipophilic interior of the helix. The interior of the helix is lipophilic because it has no polar groups facing inward, the only functional groups that are present are C—H, just as in a fat molecule. The outside of the helix is entirely hydrophilic because it contains all of the groups with dipolar moments and therefore the host is water-soluble.

Products made according to the present invention also possess thermoplastic characteristics, becoming liquid when heated and resolidifying when cooled. At room temperature, the coils of the helix are well organized and contain a guest. The yield of guests per helical volume depends upon the degree of polymerization. The fat molecules are scintillated many times per second. Logically, as the temperature increases, the guests become more active and visible, but are constantly interchanged. In addition, as the temperature increases, the molecule takes advantage of its Degrees of Freedom of Motion to absorb the energy. Eventually the vibrations due to the absorbed energy become so large that the helix attempts to unravel. Once again, this point is dependant upon degree of substitution and Degree of Polymerization with longer chains of amylose being more cumbersome and less predictable than the shorter, more manageable, hydrolyzed chains.

As long as the temperature is not pushed to the point where major molecular alterations occur, such as chemical degradation or dehydration, the chemical make-up of the molecule remains the same. Therefore, when the temperature decreases, the molecule remembers the thermodynamically-favored state and will form a helix again, thereby resolidifying and, if the guest materials are evenly distributed, the complexes will reform.

The subsequent acylation must be performed at as low a temperature as possible so as to minimize the participation of the solvating water in the acetylating reaction to achieve the highest degree of efficiency. However, pre-treating the starch at such low temperatures requires extended pretreatment times, which, in turn require excessive tankage for commercial process holding capacity, thus making low temperature soaking or pretreatment impractical.

The time requirement can be shortened so as to fit commercial circumstances by preparing a heated solution of the catalyst or soaking agent in water and mixing the purified dry starch raw material into this warm solution directly. By this method, it is possible to reduce pretreatment times from 30 hours at 2° C. and 10 hours at 20° C. down to 1 hour at 53° C. High amylose starches require higher/longer pre-soaking temperatures/times relative to their gelation points.

The pretreated solution is then cooled to prepare for penetration by the acylating agent at low temperature. The purpose of conducting the acylating reaction at low temperature is to minimize the participation of the solvating water in the penetrated solution and give the starch granules with their penetrated sodium ions as much opportunity as possible to convert acetic anhydride to acetyl groups.

The acetyl groups are also important to render the starch granule more open to hydration and subsequent enzymatic hydrolysis. The acetyl substituents tend to protect neighboring regions of the anhydroglucose chain from enzyme attack, thereby ensuring that the enzyme will not overly digest the chains. If they were overly hydrolyzed, the amylose chainlets would become too short to form complete helixes and thus lose their hosting ability.

It is important to keep the 1,6 linkages intact to a great extent. The enzyme is unable to cleave closer that 2 glucomonomers from the 1,6 linkage. This protects the amylose-like A-chains from over-hydrolysis by eliminating those zones from attack. The acetyl substituents placed along the chains then give further protection from over-hydrolysis. While it is possible to digest the amylose chains to very short fragments, this buffering protection permits extra degrees of processing freedom when the final desired product characteristics are engineered.

The present invention is dependent upon complete hydration of the starch granules after the insertion of the acetyl groups to convert crystalline regions into the more accessible amorphous regions, thus opening up the amylose molecules for enzymatic attack. It is known in the art to rely upon a shortage of water to retain the granular structure of the starch in the end product. According to the present invention, however, molecules are completely hydrated in a water soluble gel. The host molecules of the method of the present invention are uncomplexed as they have no guests remaining from the process. The hosts remain substantially unretrograded in spite of the absence of a guest molecule and this is achieved by the acetyl groups sterically hindering the super recoiling of the molecules.

Researchers in this art have found that amylopectin gels are mildly gelling in that they form soft gels over time. Addition of amylose caused a significant formation of firm gels over a short period of time. So, if the addition of amylose to maltodextrin solutions led to remarkable acceleration of aggregation process and maltodextrins can be slow gelling without the addition of amylose, then several things can be assumed:

1. when the gels or the present invention are fast gelling, it must be because of longer chain amylose;
2. this is exactly what happens when the starting temperature for the initial addition for the enzyme treatment is increased; and then
3. the amylase attacks preferentially more amylopectin groups than amylose chains at the higher starting temperatures or at least the amylose chain is not attacked as aggressively.

This is possibly because the A-chain segments of the amylopectin groups are more unraveled and more vulnerable at the higher temperatures. In other words, at higher temperatures amylopectin A-chains participate more in the enzymatic conversion and, as temperatures increase toward the terminal temperature of the enzyme and the exposure time decreases proportionately, more amylopectin A-chains are hydrolyzed than amylose. Therefore, at an 80° C. enzyme addition temperature, there is less time to hydrolyze amylose and so the resulting finished gel product is much faster gelling upon cooling. That is not to say that the amylose chains would not eventually become degraded given enough time; just that the amylettes are more vulnerable and this feature allows for that.

Analytical treatment of completed clathrates systems with a combination of endo α-amylases, such as Termamyl, and with pullulanase results in the destruction of the host molecule, the amylose, and amylettes and a release of the guest molecules, which in the case of lipids, float to the surface leaving a flocculent precipitated residue in a clear solution of short glucose chains. This residue does not react with iodine and does not complex with fats and is probably a residue of the C and B chain fragments, perhaps limited by the ester groups inhibiting the pullulanase as indicated by Biliaderis.

The process for making the host molecule involves the low-temperature modification of starch granules that have previously been impregnated or permeated with catalyst ions, such as sodium from sodium hydroxide. While the starch may be pre-soaked in a sodium hydroxide solution at low temperature to facilitate the low temperature modification, it is more commercially acceptable to effect this soaking at elevated temperatures to reduce the time requirement. Soaking temperatures on the order of about 4° C. require soaking times of up to 30 hours, while soaking temperatures of about 53° C. require 1 hour to prepare the starch granule for modification. Soaking temperature may range from a point just below the point of birefringence of the starch to 0° C. The modification should be conducted as low as possible to minimize the participation of the water in the reaction with the esterifying agent.

Granular pea starch that has had substantially all of the non-starch constituents removed is soaked in a sodium hydroxide solution to allow sodium ions to migrate uniformly throughout the granule (pH 10 at 35° C. for 4 hours). The slurry is cooled to 14° C. Acetic anhydride is slowly added while a 9% sodium hydroxide solution is used to maintain the pH of the reaction at pH 8.5 and a temperature of 14° C. Although previous references have stated a preferred pH range of 6 to 8, it has been found in accordance with the present invention that this does not produce the desired degree of uniformity. Surprisingly, dried gels made by the present method of modifying at a fixed pH of 8.5 at 14° C. may be rehydrated to re-form a solution in water and this solution may be cooked to boiling without degradation, and then may be chilled to 4° C. to form a gel which exhibits thermoreversible properties. This characteristic is an important indicator of the ability of a gel to later dissolve and participate in the chemistry of various interactions in food systems. To emphasize the distinction, dried gels made with starch modified by the prior art of maintaining a modification pH range between pH 6 and 8 form discrete, white particles upon rehydration. These re-hydrated particles do not exhibit an ability to be solubilized or melted.

When enough acetyl groups have been formed to produce a DS of 0.08 to 0.15, as calculated between the consumption of sodium hydroxide against acetic anhydride addition, the difference representing acetyl groups, the reaction is stopped and the solution neutralized. In addition to the formation of acetyl groups, sodium acetate is produced as a byproduct. The consumption of sodium hydroxide represents the production of sodium acetate. That portion of the acetic anhydride not involved in the production of sodium acetate contributes the desired acetyl groups.

The acetic anhydride will slowly react with water and this reaction rate increases with an increasing temperature of the water. Therefore, the reaction should be carried out at as low a temperature as possible. A reaction temperature between 0° C. and 15° C. is desirable. It has been found that the ideal pH for the acetylation process is temperature dependant. Lower temperatures allow higher target pH settings for conducting the modification, while higher temperatures benefit from a lower pH. See Kruger et al., *Production of Starch Acetates*. Starch: Chemistry and Technology 2d ed.", R. Whistler et al., (eds.) Acedemic Press, Inc., 1984. The optimum acetylation pH is temperature dependent: at 38° C. the optimum pH is about 7; at temperatures below 20° C., the optimum pH may be above 8.4

The modified granular starch may be washed to remove reaction byproducts and dried. However, if the material is to be hydrolyzed in the subsequent step, drying is unnecessary. Sodium acetate serves as a continuing catalyst to improve the efficiency of the acylation reaction and it is useful to recycle some of the wash water in the washing step back to the initial hydration stage to slurry the original starch raw material.

The modified starch slurry is cooked to 75° C. to 105° C. or higher. The solids may be between 1% and 40%. Different applications will require different solids contents depending on the desired concentration of available host helixes and the desired moisture content of the finished application. It is important to hydrate the starch molecule properly and thoroughly during this cooking stage to expose all available amylose chains and to unfold amylopectin branches and clusters.

The cooked gel is temperature adjusted within the temperature limits of the appropriate enzyme and enzyme hydrolysis follows. The enzyme of choice is an endo amylase, such as a bacterial amylase from *Bacillus amyloliquefaciens* with the systematic name of 1,4-alpha-D-glucan glucano-hydrolase that hydrolyzes 1,4-alpha-glucosidic linkages. The example brand name is Ban produced by Novozymes AS. While this enzyme has the ability to attack the 1,4 linkages within the amylopectin branches, this enzyme offers the additional advantage of being unable to attack the actual 1,6 linkages attaching the amylopectin fraction to the amylose, thereby offering the amylopectin bond to complement the acetyl groups attached through the modification process as barriers to complete hydrolysis. This results in the ability to hydrolyze the material aggressively while still retaining significant hosting potential in the finished product.

While the 1,6 linkage attaching the amylopectin clusters to the amylose chains are unable to be cleaved by the alpha amylase enzyme, the internal 1,4 linkages of the actual amylose-like branches of the amylopectin are vulnerable to cleaving by the enzyme and these liberated helical amylopectin fragments offer additional hosting capability for shorter chain guest molecules. The remaining intact amylopectin groups or side chain stubs attached by 1,6 linkages continue to provide a type of colloidal protection against retrogradation.

The enzyme attacks the 1,4 linkages at different sites depending on temperature. Exposure to the enzyme starting at lower temperatures yields thinner solutions with shorter chain hosts, while exposure at higher temperatures yields longer chain amylose molecules with the amylopectin branches being preferentially hydrolyzed.

This enzyme reaction is moderated by temperature or pH or a combination of both to achieve the desired end functionality. Increasing the temperature or storing the material at a disabling pH ends the reaction and the material may be used directly to produce a wide variety of products, including cheeses and the like.

Finished materials containing the mixtures of stabilized amylose and stabilized amylopectin prepared via this method will result in fluid, hot solutions with high solids contents that will resist gelation or will form meltable gels at selectable rates and degrees and be able to encapsulate/emulsify upward of 10 times their weight in lipid material.

If a shorter version of host material is desirable for special applications, the starch molecule may first be aggressively hydrolyzed to cleave a greater number of 1,4 alpha-glucosidic linkages to produce a thin, non-gelling solution. The amylase enzyme is then inactivated.

For some applications and after the production of the amylose material and inactivation of the enzyme, it may be desirable to provide a pre-installed guest molecule to enhance the mechanism of the host gel in its final product application. Suitable guests may include any hydrophobic material that is compatible with the material to be treated. Butter oil or short chain fatty acids for flavor enhancement are but two of the myriad of possibilities. Pre-installed guests are especially desirable when the dextrin gel is being incorporated into the target mass at low starting temperatures. The existence of a starter guest molecule multiplies the ability of the gel to infiltrate the molecular structure of the mass and acts as a buffer to retard the aggressive nature of the pure dextrin gel. While it is true that guests are not attracted by ionic forces to the hydrophobic core of the host molecule, the aggressive mixing techniques necessary to infiltrate tough, cool lipid bearing masses may create a prematurely high introduction ratio. This may create a counterproductive excessive division of globules of fat in the target mass. Pre-existing guests seem to increase the mixing tolerance for difficult substrates such as cheese. The pre-installed guest can also be employed to form a sort of scaffold or lattice effect to provide a more rigid structure in which subsequent short chain guests may be stabilized. Saturated mono- and di-glycerides for example can provide this re-bar type structure.

The hosting capacity of the molecule has a sort of stoichiometric definition. Theoretically, amylose molecules of more than 6 or 7 glucomonomers may act as hosts to many hydrophobic materials, but most amylose material is much larger and in practice there is always some kinking involved in these longer chains of amylose. This, then, limits the volumetric exposure of the host, as longer, straight segments may not present themselves as vacant cavities. Medium length chains, such as those of the amylettes derived from the amylopectin fractions of, for example, peas, with a cleaved glucomonomer chain length of perhaps 15 to 24, offer a high degree of vacancy per mole. Nevertheless, a solution of these molecules can be described as having a certain capacity to host a relative number of guest molecules. This stoichiometric ratio may be shear dependant as the success of guests in finding vacant hosts depends on the intimacy of their introduction. When complexes of guests and hosts reach the stoichiometric balance, as adjusted by the shear factor applied to that particular mixture, they transition from a molecular dispersion to a more traditional emulsion with the guest/host complexes acting then as emulsifiers. In this super-phase, the additional guests are not clathrated or complexed; rather, they are emulsified by the guest/host complex itself, but outside the host and in an oil-in-water environment. This accounts for the unusually high oil management capacities of this system because it is a combination of first dispersion and then emulsification.

It should be noted, however, that for applications that rely upon the guest being occluded or hidden, for example, in pharmaceutical applications to protect sensitive components from premature degradation, it is important not to exceed this stoichiometric factor as guests that exceed the stoichiometric definition may be exposed.

It is interesting to note that when a clear guest, such as melted paraffin or a siloxane product, is introduced into a clear or slightly opaque solution of host material, the resulting clathrate is always white. In fact, this can be used as an indicator of the formation of the clathrate. Colorless oils will usually form pure white complexes with the host of the present invenintion. This optical effect can be observed with tri, di and monoglycerides, fatty acids, and a variety of other hydrophobic materials.

Complexes formed with this mechanism exhibit unusual specific gravity. While the host macromolecule has a density greater than water, it is the combined characteristic of the complex, including the guest, that determines the final density. Typically, complexes of lipid guests in medium-chain hosts will rise to the top of a centrifuge tube during centrifugation, while virgin amylose, should there be any, and amylopectin dross, the remnants of the amylette harvesting process, drop to the bottom of the tube. The fate of the final complex therefore may be predetermined, in a way, by selecting the desired degree of hydrolysis of the amylose fractions to match the molecular weight of the intended guest.

This observation has led to the discovery of a convenient method of separating potential hosting materials from non-hosting amylopectin fragments by introducing a low density hydrophobic guest, such as hexane, to the slurry, centrifuging the resulting lighter guest/host complex from the denser amylopectin dregs, and evaporating and distilling off the volatile hexane guest, leaving virgin, stabilized, nanotubes of pre-engineered amyloses in solution.

The liquid host material may be spray dried, freeze dried, or co-dried with companion materials to produce a powder with unusual fat management capabilities.

Solutions prepared by the method of the present invention, even if they have been reconstituted from their dried state, will form complexes with guest molecules at cold temperatures under the proper conditions. There is no longer any need to rely on co-cooking or temperature related convolution of the host around the guest.

The advantages and the important features of the present invention will be more apparent from the following examples.

EXAMPLES

Example 1

1. Prepare a 35% solids solution by slurrying purified pea starch in warm water to which has been added sufficient sodium hydroxide to produce a slurry with a pH of 10 and maintain by stirring and temperature control for 3 hours at 48° C.
2. Agitate well during this step. Cool the reaction to maintain 10° C. Add acetic anhydride at a constant rate while maintaining the pH of the slurry at pH 8.5 with added 9% sodium hydroxide solution. Add an amount of acetic anhydride that, when corrected for sodium hydroxide consumption, provides for a starch with a Degree of Substitution of 0.10. Maintain the temperature below 15° C. Dilute and wash the starch.
3. Make a 20% solids solution, pH 5.8, with water and a suitable acidulant, such as HCl. Heat to 95° C. to 105° C. and hold for 2-5 minutes.
4. Cool to 73° C. (the selected beginning of the temperature range for the following enzyme).
5. Treat with a suitable amount (0.00067%) of Ban enzyme and hold until the desired viscosity is attained. Heat to 92° C. to 105° C. to inactivate the enzyme. The heating time is typically 15 minutes to reach the target temperature. Combinations of enzyme dosage and time to reach the terminal point of the enzyme may be inversely varied to achieve the target finished product. Cooked slurry will start out as a very viscous mass and eventually thin to a thin fluid viscosity. The factors for selection here are that the gel is thermoplastic and will behave as a cheese when heated. The shorter the hydrolysis time, the longer the amylose, the more the film forming, and the longer the melt characteristics, the shallower the melt/temperature slope. The longer the hydrolysis, the shorter the amylose, the less film forming, and the thinner the melt characteristics, the steeper the melt/temperature slope.
6. The product may then be packaged as a hydrated gel or dried to a powder for future re-hydration.
7. If a pre-installed guest is desirable, then, prior to drying, add the starter guest lipid component. This increases the efficiency of the host molecule. Homogenization is not necessary, as the gel will hold the guest fat with even mild agitation; however, homogenization will result in a more aggressive mixture. In the case of preparing an ingredient for cheese manufacturing, butterfat is added and may be added at a level of 1% to 40% of the total mass. 10% is often a useful level. Butter flavors may also be used alone or in combination with butter. The short chain fatty acids involved in butter flavors are ideal guest molecules. The guest may be combined immediately or may be added at some future time. The gel will remain fluid for a period of time after melting and a fluid guest may be added at any temperature while they are fluid. The guest may also be added as a solid to the solid gel at cool temperatures, if desired, by providing enough energy to combine the two fractions thoroughly. With time, the guest molecules will migrate to the available host cavities to form molecular dispersions.

Example 2

1. Three thousand pounds of isolated pea starch are added to 630 gallons of water that has been prepared with 4.5 pounds of caustic soda beads and preheated to 45° C.
2. The slurry is allowed to soak at 45° C. for 2 hours and then cooled to 10° C.
3. Acetic anhydride (220 pounds) is added over the course of two hours concomitant with 1100 pounds of 9% caustic soda solution so as to maintain the pH of the slurry at approximately 8.5.
4. When the required reactants have been added, the flow of caustic soda solution is stopped and the acetic anhydride is allowed to continue until the pH reaches 6.0.
5. The reacted starch slurry is washed using a liquid hydrocyclone array to extract a substantial portion of the dissolved reaction byproducts.
6. The washed reacted starch slurry is diluted with clean water to 22% solids.
7. The diluted slurry (220 gallons) is cooked in a steam jacketed, scraped surface kettle to 92° C.
8. The cooked solution is cooled to 72° C.
9. Three grams of Ban enzyme is diluted in 400 grams of distilled water and then added to the cooked solution with the mixer operating at medium high speed.
10. The enzyme-treated, pre-cooked solution is re-cooked to an end point of 92° C.
11. The re-cooked, thinned solution is dried in a spray drier.

12. This produces a reconstituted 20% solution that, when heated to boiling in a microwave, produces a hot gel with medium thick viscosity and forms a firm gel after storage at 4° C. for 4 hours.

Example 3

1. Isolated pea starch (770 pounds) is added to 165 gallons of water at 10° C. that has been prepared with 300 grams of caustic soda beads.
2. The slurry is allowed to soak at between 15 and 20° C. for 10 hours.
3. Seventy-two pounds of acetic anhydride is added over the course of 2 hours concomitant with 450 pounds of a 9% caustic soda solution so as to maintain the pH of the slurry at approximately 8.3.
4. When the required reactants have been added, the flow of caustic soda solution is stopped and the acetic anhydride is allowed to continue until the pH reaches 5.7.
5. The reacted starch slurry is diluted with 400 gallons of water and allowed to settle. After six hours of settling, the supernatant is siphoned off to remove dissolved reaction by-products.
6. The washed reacted starch slurry is diluted with clean water to 22% solids.
7. The diluted slurry (220 gallons) is cooked in a steam jacketed, scraped-surface kettle to 92° C.
8 The cooked solution is cooled to 72° C.
9 Ten grams of Ban enzyme is diluted in 400 grams of distilled water and then added to the cooked solution.
10 The enzyme-treated, pre-cooked solution is re-cooked to an end point of 92° C.
11 The re-cooked, thinned solution is dried in a spray drier.
12 This produces a reconstituted 20% solution which when heated to 95° C. produces a hot gel with low, water-like viscosity and forms a medium firm gel after storage at 4° C. for 24 hours.

The slow gelling characteristics of Example 3, with an enzyme addition temperature of 72° C., indicates the presence of shorter amylose chains, but the increased fat-holding ability indicates that starting the enzyme treatment at a lower temperature, therefore giving the reaction more time, yields a shortening or division of liberated A-chains. The fact that these liberated A-chains still have an iodine blue reaction, indicating chain length of over 6 or 7 glucomonomers and they still hold fat, even after prolonged enzyme exposure, confirms that the endo-enzyme degradation is limited by the ester groups.

Example 4

1. Isolated pea starch (770 pounds) is added to 165 gallons of water at 4° C. that has been prepared with 300 grams of caustic soda beads.
2. The slurry is allowed to soak at between 4 and 8° C. for 24 hours.
3. Seventy-two pounds of acetic anhydride is added over the course of two hours concomitant with 450 pounds of a 9% caustic soda solution so as to maintain the pH of the slurry at approximately 8.3.
4. When the required reactants have been added, the flow of caustic soda solution is stopped and the acetic anhydride is allowed to continue until the pH reaches 5.7.
5. The reacted starch slurry is diluted with 400 gallons of water and allowed to settle. After six hours of settling, the supernatant is siphoned off to remove dissolved reaction by-products.
6. The washed reacted starch slurry is diluted with clean water to 22% solids.
7. The diluted slurry (220 gallons) is cooked in a steam jacketed, scraped surface kettle to 92° C.
8. The cooked solution is cooled to 78° C.
9. Four grams of Ban enzyme is diluted in 400 grams of distilled water and then added to the cooked solution.
10. The enzyme-treated, pre-cooked solution is re-cooked to an end point of 92° C.
11. The re-cooked, thinned solution is packaged as a warm, viscous gel at 50° C. in plastic liners in 40 pound corrugated boxes and then placed in a cooler for chilling.
12. This produces a cold, hard gelatin-like gel that, when warmed in a microwave oven at 100% power to the boiling point, produces a hot gel with a thick viscous characteristic and which re-forms a hard gel after storage at 4° C. for 1 hour. This gel re-melts again in repeated microwave treatments and repeated chill heating cycles.

Example 5

1. Isolated pea starch (770 pounds) is added to 165 gallons of water at 4° C. that has been prepared with 300 grams of caustic soda beads.
2. The slurry is allowed to soak at between 4 and 8° C. for 24 hours.
3. Seventy-two pounds of acetic anhydride is added over the course of two hours concomitant with 450 pounds of a 9% caustic soda solution so as to maintain the pH of the slurry at approximately 8.3.
4. When the required reactants have been added the flow of caustic soda solution is stopped and the acetic anhydride is allowed to continue until the pH reaches 5.7.
5. The reacted starch slurry is diluted with 400 gallons of water and allowed to settle. After six hours of settling the supernatant is siphoned off to remove dissolved reaction by-products.
6. The washed reacted starch slurry is diluted with clean water to 22% solids.
7. The diluted slurry (220 gallons) is cooked in a steam jacketed, scraped surface kettle to 92° C.
8. The cooked solution is cooled to 72° C.
9. Four grams of Ban enzyme is diluted in 400 grams of distilled water and then added to the cooked solution.
10. The enzyme-treated, pre-cooked solution is re-cooked to an end point of 92° C.
11. Butterfat (120 pounds) is added to the hot solution at normal mixing speed. The butter melts into the solution and forms a clathrate without any additional shear or agitation and no free fat appears on the surface.
12. The re-cooked, thinned, butter-clathrated solution is packaged as a warm, somewhat viscous gel at 40° C. in plastic liners in 40 pound corrugated boxes and then placed in a cooler for chilling.
13. This produces a cold, firm butter-like gel that, when warned in a microwave oven at 100% power to the boiling point, produces a hot gel with a slightly viscous characteristic without any evidence of free fat and that re-forms a firm buttery gel after storage at 4° C. for 12 hours. This gel re-melts again in repeated microwave treatments and repeated chill/heating cycles.

Example 6

Formation of a Complex with Soybean Oil

Thirty grams of the low viscosity powdered emulsifying gel prepared in Example 3 is dispersed in 500 mL water at 10°

C. in a 1 liter beaker. The powder is dissolved into solution with the use of a Braun electric hand mixer, a very low shear device.

Three hundred grams of soybean oil are added to the beaker without mixing. The soybean oil floats on top of the solution.

The Braun hand mixer is submerged to the bottom of the beaker and turned on. The mixer is angled so that the vortex draws the top oil fraction down into the mixer.

When the entire oil layer has been incorporated, it is evident that no free oil is visible. Additional mixing develops a more complete molecular dispersion and emulsion. After one minute of mixing, a 25 mL portion of the dispersion is mixed into cold tap water and a homogeneous milky solution is created with no evidence of free oil.

This example shows the unusually high oil holding capacity and the low shear necessary to form a molecular dispersion of this invention.

Application of this Technology to Cheese Manufacturing

Attempts to use amylose or starch to manage fats have previously taken the path of
(a) binding chemical residues onto certain sites on the starch molecule to bind onto fats, or
(b) creating one-time amylose/lipid complexes in which the lipid is co-cooked with the gelatinizing starch and wrapping the lipid in the unraveling amylose where after the amylose retrogrades to form a permanent irreversible, non-meltable complex.

The preparation of irreversible amylose or starch lipid complexes prepared by co-cooking as described above and then mixing that ingredient into the milk phase of the cheese making process (at the very beginning of the process) is known in the art. The present invention, on the other hand, involves proteins that are the result of the coagulation proteins after the cutting of the curd.

Other known art describes methods to add fillers, such as starch, to cheeses, but the guest/host approach is not used, and it appears that the traditional calcium binding mechanism of phosphate salts and citrates is relied upon to tame the proteins and enable the mixing of starch into cheese. The known art does not use the starch in gel form and as a result does not enable, nor does it discuss, the significant cost reduction benefit of the present invention.

The calcium-binding approach to processed cheese is the time-honored approach to cheese protein management. It is so entrenched and widely used that the unique products produced by reducing the stretchy effect of protein calcium bonds actually have their own standards of identity and their own end-food-product applications. The technology of the present invention permits the processing of cheese while retaining the natural character of the proteins, thereby allowing for the production of processed mozzarella with all of the characteristics of natural traditional mozzarella. The pasty, gummy texture of normal processed cheese is avoided.

The technology of the present invention also opens up the hitherto impenetrable virgin cheese mass to permit the addition of other functional ingredients. These ingredients can include calcium chloride, transglutaminase, and other enzyme systems.

Calcium is normally the nemesis of cheese processors. With the present system, it is even desirable to add calcium to the cheese mass so as to extend the strength of the proteins as much as possible and thereby permit the most aggressive dilution for economic purposes. The protein is the single most expensive component of the mozzarella cheese product and the ability of this technology to reduce the content of protein while maintaining or indeed increasing its overall effect is very attractive economically. Adding calcium to encourage additional calcium protein bonds is contrary to the art of traditional cheese processing, but can be employed within the scope of the present invention.

Similarly, hitherto-unavailable approaches may be taken to the use of enzymes, such as transglutaminase, which may be introduced to the cheese mass inside of the dextrin gel as an additional functional ingredient. This enzyme has a significant effect on cross linking the proteins in a cheese mass and therefore affects the economics favorably, as well. Known means for using this enzyme have been restricted to adding it to the milk at the beginning of the cheese making process or by pre-treating whey proteins with it before adding them to the milk at the beginning of the cheese making process. Adding it at the curd cooking stretching stage or to the finished young cheese is not known to have been disclosed or suggested in the art.

This chemistry plays an important dual role in mozzarella cheese. Fresh mozzarella has a protein matrix composed of a high proportion of hydrophobic, or more importantly, lipophilic groups. Over time, proteolytic enzymes fragment these proteins, thereby changing the nature of the protein matrix and having the effect of rendering the cheese more meltable. The changes in the proteins have to do with a gradual hydration and a reduction in the relative influence of the lipophilic groups or an increase in the effectiveness of the calcium-containing hydrophilic ends.

One of the keys to manipulating the mozzarella characteristic has to do with modifying the distribution of the fat.

The processed cheese industry uses melting salts or emulsifying salts including phosphates or citrates to sequester the calcium ions, which on one hand reduce the solubility of the proteins and on the other hand form the power base for the strength of the protein interactions. Once these calcium ions are diverted from their protein-complexing role the proteins are more vulnerable to hydration using energy in the form of high temperatures. Unfortunately, proteins that have been chemically and thermally altered with this processing system are unable to be restored to their previous character and cannot be used for traditional mozzarella applications, for instance, those that require the calcium ions to participate in providing the typical mozzarella stretch.

The technology of the present invention is capable of reassigning the role of traditional emulsifiers, such as the native proteins in cheeses, from one of primary emulsifiers and secondary structure builders to one of primary structure builders and secondary emulsifiers. The subject host molecule takes over the primary role of emulsification and, by dividing the fat globules, makes the protein more intimately exposed to the various bound waters of the host molecule. This controlled accelerated hydration permits the immediate formation of additional protein-protein linkages, thereby reducing the amount of protein needed to obtain stretch and strength and at the same time stabilizing the fat to minimize separation. The combination of all of these effects reduces the ingredient cost of cheese by as much as 15% and returns a greater than usual margin for the ingredient molecule.

The fat-complexing function of the helical lipophilic core of this stabilized amylose divides the pools of fat that serve as focal points for the lipophilic ends of the proteins. The traditional cheese making process does not involve a great deal of shear and, as a result, the fat globules in normal cheese tend to be rather large instead of the aggressive emulsions that one might find in mayonnaise for example. The modified amylose has the ability to intrude upon that fat/protein matrix and effectively divide the fat pool into smaller and smaller bodies. This has the secondary effect of dividing the protein molecules or strands into more numerous, more finely distributed groupings. These finer groupings are more vulnerable or accessible to water hydration. While the opposite ends of the proteins are hydrophilic, the localization of the lipophilic forces around fat globules normally prevents the migration of water into proximities near enough to achieve hydration. This is where the amylose molecule, with its outer mantel of bound water on its hydroxyl groups and the associated secondary and tertiary water, plays a key role because, effectively, the amylose acts like a water soaked sponge working its way into the interstitial zones and helping to hydrate the proteins as they become available through the action of the amylose molecule on the redistribution of fat.

Therefore, as the molecule reduces the size of the fat droplets and increases the number of lipid zones, it also provides a source of bound, partially bound, and loosely bound water to satisfy the requirements of the newly divided hydrophilic parts of the proteins. All of this happens without destroying the important calcium/protein interactions. It is thus reasonable to expect that original functionality can be retained. It is also reasonable to expect that the material balance can change, since a new component and additional water are incorporated with this technology. Further, since the molecule increases the system's ability to deal with or hold fat, more fat can be added.

Accordingly, what results is a new tool for manipulating final characteristics. Additional calcium or similar ions can be added at the appropriate stage, cream extracted from the cheese whey can be added back to the cheese to improve yields, enhance flavor, and fine tune melting properties. Butterfat, alone or complexed in the molecule, can be added to achieve finished baked characteristics. Additional enzymes, such as transglutaminase, can be used to finish the process to affect final product characteristics. The net effect is to produce a marketable cheese earlier, have more control over the final characteristics, and improve the economics through addition of less expensive components.

This is achieved through the introduction of the appropriate amount of the molecule material either as a gel or as a dried powder into the cheese and then heating the cheese to temperatures through the melting point of the fat component. The appropriate amount depends on the age of the cheese. New cheese curd may require the introduction of the dextrin gel in stages as the fat content is slowly divided allowing time for hydration of newly exposed zones. Older cheeses may have the entire targeted amount of the ingredient introduced at one point at the first blending and formation of paste. For new cheeses, the gel ingredient may be introduced in stages with the first stage introduced in such a way as to form a paste or intimate mixture of the ingredient into the cool cheese curd after which the product is warmed to begin melting. Too much of the ingredient at this stage can result in an over-emulsified product having a soupy texture. Conversely, too little of the dextrin gel ingredient will result in a bucky cheese with free liquid. Once the initial melt has been achieved, resulting in a smooth homogeneous mass, more gel ingredient in combinations of whey cream, ingredient, and, perhaps, butter may be added gradually with continuing heating and stretching. The cheese may be worked to develop the proteins up to a temperature of approximately 150° F. to 170° F. The degree of work and the final pH of the cheese affect the hardness and shreddalbility of the chilled product.

Alternatively, the dextrin gel ingredient may be manufactured so as to have a high pH. This helps to raise the pH of the cheese mass and make the proteins more vulnerable to intervention. After a homogeneous heated mass has been produced, the pH may be reduced by the use of various food acids to a desirable level. In this way, by increasing the initial pH to 6.3 to 7.5 with sodium hydroxide/dextrin gel for the initial mixing and heating stage and then reducing the pH to 5.2 to 5.6, a superior cheese product may be made from even the youngest brined cheese.

Different cheese culture systems produce cheeses with different characteristics at various stages of aging and as a result the ingredient system must be tailored specifically for the target cheese. This tailoring process also applies to the production of different grades of finished product to suit a variety of customer needs.

Samples of "tempered" or modified cheese prepared in accordance with the present invention have been made with various cheeses and have been reported to be "superior" in all aspects. These aspects include, but are not limited to, hot stretch, color, bite, texture flavor, melt, rate of hardening on re-cooling, shreddalbility, hot flow, and browning. Variations of formulae and processing variables may be used with the technology of the present invention to predetermine any and all of the foregoing characteristics.

A paste or intimate mixture should be made of the cheese and the dextrin ingredient. A steam jacketed mixer, or a direct steam-injected cooker with a system of screw augers, or a sequential combination of these devices should be used to melt the cheese/gel mass and work the cheese into a cohesive, stretchable mass.

As alluded to above, the age of the mozzarella is a very important factor to use in determining the proper dosage and sequence of dosing the gel into the mozzarella. Aged cheeses already have their butterfat globules divided to a certain extent by the natural action of the remaining cultures in the cheese and by the normal migration of water and the hydration of proteins. For these aged cheeses no special precautions must be taken and all of the desired target dextrin gel may be blended into the mozzarella at the beginning of the process. Indeed, if the cheese is old enough, for example 21 days, the cheese may be melted and the dextrin gel added after or as the mass reaches target temperature.

Younger cheeses may also be used as starting material. Cheese curd may be taken before the traditional cooking or stretching stages and used as starting material. In all cases, an evaluation of the condition of the proteins must be made to ascertain the proper dosage and sequence of dosage. Young curd that has not yet been cooked and is fresh may be dosed aggressively as the proteins have not yet established a strong hydrophobic position. Cheeses that have been cooked and stretched must be dosed more cautiously. Failure to form a complete paste prior to introduction of the heat or incorporation of too much or too little of the dextrin gel can result in either an over-emulsified or under-absorbed condition.

The "over-emulsified" condition takes on the appearance of a cheese soup in which no protein structure is observed and the cheese mass acquires a very thin consistency. This results from an overly aggressive division of the lipid pools or globules. Under the right conditions, addition of an amount of finished cheese to this pool can result in a reversal of the over emulsion. The age or stage of process and the type of culture system used in the making of the original curd will dictate the necessary dosage and sequence. Generally, it is desirable to conduct a series of test batches to determine the type of dosage that will be required to deal with a particular circumstance. This optimal profile will remain valid for subsequent batches and may be used for scale-up purposes.

The "under-absorption" condition results when the proteins are allowed to interact too aggressively without sufficient water to buffer the interaction. As opposed to over-emulsification, this under-absorbed condition takes on the appearance of well-defined thin threads of overdeveloped proteins. The protein masses continue to aggregate giving the appearance first of cellulite-type islets within the cheese, later developing into hard balls of concentrated protein. During this phase, free whey liquids are expelled. This condition results from an insufficient amount of dextrin being added at the primary or pasting stage, resulting in an insufficient division of butterfat globules. This condition is reminiscent of normal attempts to melt mozzarella at a very young age. If addressed early enough, the condition can be reversed with the addition of the corrected amount of dextrin gel.

Mozzarella that is cooked, brined, and between one and four days old is the most sensitive to dosage with the dextrin gel. The sensitivity of the four-day-old cheese is probably related, in part, to its salt content. Example formulas used to make these test cheeses resulted in as much as a 30% dilution of the cheese with dextrin gel and it is reasonable to assume that the gradual dilution of the salt during "finishing" modifies the functionality of the proteins and might result in apparent sensitivity to the changing characteristic of the brined cheese.

The purpose of this dextrin gel ingredient in the cheese is to provide an inexpensive (high water) meltable ingredient that will act as a processing aid to handle the fat content. The fat content issue has multiple dimensions:

(1) This technology can be used for extending full fat cheese by allowing for added low cost replacement or filler fat in which case the fat complexing ability of the dextrin gel tames the fat component and eliminates oiling out.

(2) The dextrin gel converts the small existing fat content in low fat or fat-free cheeses into the complexed form, in which case the flavor profile of the fat is enhanced by virtue of the molecular dispersion that the dextrin encourages, and the individual flavor components are highlighted, creating a more rewarding fat reduced cheese product.

(3) The dextrin enables the introduction of lower cost ingredients to reduce cost.

In all cases, the amylose component forms a film on the palate when the cheese is eaten. That film contains complexed fats and thereby enhancing the flavor perception of the system in both full fat and fat-reduced cheeses. When eaten alone or as part of an entree, such as pizza, the enzymes in the saliva slowly hydrolyze the amylose whereupon the flavorful fats are released, whereby the flavors of the cheeses made with this product are longer lasting and more satisfying.

The foregoing aspect of the present invention can be achieved by first chopping a suitable mixture of cheeses into shreds or pieces and adding any discretionary ingredients, such as maltodextrin, salt, caseinates, and the like to the chopped cheese mixture. Melting salts, such as disodium phosphate or sodium citrate, may be added, but are normally not needed since the melting characteristics can be substantially controlled by the engineering of the subject dextrin product.

Other chemicals may be added, such as acidulants to influence the remelting and shreddability characteristics of the cheese. Ironically, calcium ions, e.g., calcium chloride or other calcium source, may be added to increase the strength of the cheese proteins. This is contrary to existing cheese processing teaching, where calcium must be removed from active participation to allow the proteins to be melted. Also, enzyme systems, including transglutaminase and whey/glucose oxidase/catalase systems, may be added to strengthen the proteins.

A portion of the full fat cheese used in this process may be pre-treated with a dextrin gel which disperses the fat more uniformly making the fat more available to a lipase enzyme treatment, which further contributes flavor to reduced fat cheeses. In this case, the pre-treated cheese may be heated to inactivate the lipase enzyme prior to being incorporated into the main process.

Other enzyme systems may also be added at this point. Enzymes, such as lactase to reduce the lactose content of the cheese, are useful to control the browning characteristics of the finished cheese product. Glucose oxidase may be added to convert the resulting glucose to gluconic acid. Catalase enzymes can convert the resulting hydrogen peroxides to oxygen and strengthen the protein matrix by converting free sulfhydryl groups to disulfide linkages. Transglutaminase may be added to cross-link proteins, thereby further strengthening the protein matrix.

Secondly, the hydrogel host product of this invention is mixed in with the chopped cheese mixture at ambient temperature. The sequence and amounts of the addition of the dextrin depends on the age of the cheese as earlier discussed. The dextrin may be stored in its original hydrated form for a significant period of time at refrigerated temperatures as a gel. It will remelt on heating. Alternatively, the dextrin may be spray dried and mixed in with the cheese mass followed by the addition of water.

Next, the cheese mass is heated to 60° C.-70° C. and mechanically mixed to fully incorporate the ingredients and to work the native and added proteins, if any, to develop strength.

An example of a cheese manufacturing formula using this invention is as follows:

| | | |
|---|---|---|
| 1. Mozzarella cheese, Low Moisture part skim, 2 days old. | 3,000 g | 75.2% |
| 2. Salt | 24 g | 0.6% |
| 3. Hydrated host gel<br>Form paste<br>Mix/Heat to about 130° F. (about 54° C.) | 220 g | 5.5% |
| 4. Hydrated host gel 2 (melted)<br>Mix/Heat 130-140° F. (54-60° C.) | 180 g | 4.5% |
| 5. Whey Cream (33.15% fat)<br>Mix/Heat 130-150° F. (54-66° C.) | 150 g | 3.8% |
| 6. Hydrated host gel 3 (melted)<br>Mix/Heat 130-150° F. | 90 g | 2.2% |
| 7. Butter Fat | 120 g | 3.0% |
| 8. (Optional) Transglutaminase enzyme mixed with butter<br>Mix/Heat 130-150° F. | 1 g | 0.025% |
| 9. Water | 200 g | 5.0% |
| 10. Mix/Heat 130-170° F. (54-77° C.) knead to develop protein elasticity & strength | | |

This procedure was used with cheese of different ages. The pasted cheese mass melted well without the characteristic formation of rubbery casein masses and free whey. Mixing was done in a Hobart mixer with a steam-jacketed bowl. If mixing is inefficient or cannot incorporate the dextrin gel efficiently into the cheeses mass, a localized under-absorbed condition may result. That situation may be recovered with the addition of additional dextrin gel at the proper time. The batch may taken to a higher temperature 165-167° F. (74-75° C.). The finished cheese product does not appear to suffer from the higher temperature and subsequent baking tests showed that the chilled, shredded sample of this cheese had superior baking characteristics. This higher temperature is commercially important, as the product with more heat treatment has less enzymatic activity remaining and therefore less storage related quality issues.

It is desirable to use this technology to "finish" the cheese as close to the time of original manufacturing as possible because the proteins in fresh cheese are the strongest and offer the most opportunity for dilution for optimum economics.

Alternatively, this technology involves taking finished cheese loaves of suitable age and retro processing that cheese to upgrade the functionality and economics. That remains a good use of this technology; however, the current technology is also capable of taking cheese directly from the curd stage or the cooker and finishing it prior to shredding.

This technology is capable of successfully finishing cheese curds taken prior to the cooker. This represents a significant process advantage because of reduced processing costs, higher capacity, and lower inventory loads. However, the fresh curd normally has higher whey content, which is normally leeched out during the brining stage. Bypassing this stage increases the whey content for this "curd intercept" approach. Traditional cheese processes attempt to balance off the aggressiveness of curd cutting with the need to preserve yield. This results in certain acceptable whey content in the cut curd. Some of this whey is then normally washed out of the cheese mass during the cooking stage. This is followed by a subsequent migration of additional whey out of the cheese during brining.

The process of the present invention allows whey cream and fines to be readily recombined into the mixing/cooking/kneading stages. This then enables the cheese curd to be more aggressively harvested and the original curd can be processed more aggressively, expelling more whey in a more aggressive cutting stage and then proceeding directly to the present process, thereby bypassing the traditional cooking stage.

The appropriate level of salt can be added upstream at the mixing/pasting stage, thereby replacing the less controllable brining stage. Varying saltiness is a major issue with the traditional mozzarella cheese making process. Since salt is added as needed to the cheese mass before or during cooking the method or the present invention eliminates this unpredictable brining stage.

Cooling can be achieved in a chilling tunnel after which shredding can take place in line. This process should result in a lower capital cost, higher capacity, lower operating costs, fewer process and quality variations, reduced ingredient cost of production, lower inventory loads, more control over final functional characteristics, and more efficient use of by-products.

It is very important to note that this technology may be used to extend cheese by as much as 40% and, at the same time, produce a mozzarella that actually has higher quality with more desirable attributes, in every respect, than traditional mozzarella.

The following is a discussion of the basic manufacturing considerations including the addition and mixing zones as well as indications of the types of control systems to automate the addition of the various ingredients.

The Preparation Stages

The starting cheese material (temperature less than about 120° F., i.e., about 49° C., or below melting)
Curd or
Cooked cheese pre brining or
Brined cheese.

The Pasting
Ricing or other size reduction
Pre-Mixing—e.g. ribbon blender, mixing screw
Dextrin gel 1 addition
Salt
Enzymes
Pasting—Plate mill, etc. or alternatively the ribbon blender may be set at discharge mode with the discharge gates closed to force the cheese mass to mix more vigorously.
Screw pump/conveyor linked to mixer.

The Mixing

The mixer is a multi zone, steam/cool water jacketed closed mixer with intermittent paddles to provide strain testing zones utilizing strain gauges to measure the elastic nature of the cheese mass throughout the mixing/heating/addition stages. Conductivity, pH, temperature, and specific ion measurement can be taken at various points to characterize the changing nature of the cheese as it flows through the process to control the correct levels of addition of each of the ingredients and to determine the exact characteristic of the final cheese product. The measurements are fed to a programmable logic controller to automate the addition of ingredients and application of temperature to match particular product specifications.

1. The first stage heating mixing
   The measurement
   The addition of Dextrin gel 2 in stages
2. The second stage—conditioning and cream addition
   The measurement
   The addition of Cream and Dextrin gel 3 as necessary
3. The third stage—Butter fat addition, addition enzymes
   The measurement
   The addition of Butter and enzymes.
4. The fourth stage—Additional water
   The measurement
   Addition of the finishing water
   Measurement to confirm finishing characteristics.
5. Extrusion into packages for cooling or to ribbon chiller, Alternative Manufacturing Method 2 Using Dry Emulsifying Dextrin Powder and Cooking in a Cheese Processor:

| | |
|---|---:|
| Mozzarella Cheese Curds | 1500 lbs |
| Emulsifying Dextrin Powder | 64 lbs |
| Anhydrous Butter | 80 lbs |
| Salt | 2 lbs |
| Non fat dry milk | 44 lbs |
| Water (added at cooker, batch equivalent) | 200 lbs |
| Total | 1,890 lbs |

Grind cheese and pneumatically convey to double screw blender.
Add dextrin powder.
Add non-fat dry milk for flavor augmentation.
Add salt.
Add anhydrous butter
Mix to a paste by mixing while in discharge mode with the exit gates closed until a smooth paste is formed.
Add a portion of the cheese paste to the twin screw, steam injected, cheese cooker
Add Water proportionate to the cooking batch
Inject steam until cheese mass reaches a minimum of 132 deg F. ideally 150 to 160 degrees F., with the mixing screw speed at 100 RPM.
Continue to operate screw to stretch the cheese for 2 to 3 minutes.
Dump into holding tank and pump into molds.

The following is a description of a few of the emulsifying dextrin gels that may be produced and a brief discussion of their characteristics and methods of use.

Medium Chain. This product is the primary gel to be used at the first stage of the process as the initial dose in the cheese according to the sample starting formula. It may be used as the only gel in the formula at all stages or in combination with secondary doses of the any or both of the following gels. It will melt easily and has the highest fat management ability.

Short Chain. This product has a low melt point and may be used at the second or third stages of the process to increase spread and reduce the melt temperature of the finished mozzarella. This probably won't be used at a rate higher than 2 to 4 percent of the finished cheese weight.

Long Chain. This product is exceptionally strong and is used to manage unusually high free-water situations in the second or third stages. It may also be used at a low percentage in the original grind in combination with the primary gel, 450e. Generally 700eL will strengthen the cheese, giving it a longer, chewier texture, and increase the melt point to decrease melt and flow. 700eL has a high melt temperature and should be pre-melted to 95° C. with agitation. It may be diluted with some of the additional formula water for easier handling.

The following formulations describing methods of the use of the guest/host complex structure described herein are merely examples of many possible recipes. Those skilled in the art will realize that subtle variations in ratios can make one product more desirable for some applications than others. The formulas stated here are not necessarily the only ratios available, nor are they necessarily the best, but rather they are presented as starting points that demonstrate the utility of the underlying invention.

Formulations Using the Technology of the Present Invention:

| Cream Cheese Analogue | |
|---|---|
| Partially Hydrogenated Corn Oil | 22.00 lbs |
| Emulsifying dextrin gel 20% solids | 20.00 lbs |
| Liquid Premix | |
| Water | 16.14 |
| Non fat dry milk | 1.29 |
| Bravo 500 Whey Protein Concentrate | 1.61 |
| Calcium Caseinate | 1.41 |
| Maltrin 100 Maltodextrin | 3.38 |
| ButterBuds Manchego Cheese Flavor | 0.20 |
| Salt | 0.45 |
| Lactic Acid 88% | 0.35 |
| Firminich nat. Flavor 73161202SD | 0.01 |
| Firminich art. Flavor 598259S16 | 0.01 |
| Total | 66.85 lbs |

Premix liquid premix ingredients.
Melt emulsifying dextrin gel in steam jacketed kettle.
Agitate with propeller type mixer, add corn oil to melted dextrin gel.
Add liquid premix to dextrin/oil mixture.
Add lactic acid and adjust to pH 4.65 as needed.
Add additional flavors.
Homogenize at 75° C. with a two stage homogenizer at 500/2500 lbs.
Package and chill.

| Blue Cheese analogue | |
|---|---|
| Fleischmann's Corn Oil Mixture | 200 g |
| Emulsifying dextrin hydrogel 20% solids | 300 g |
| Cargill Phyto Sterol Ester | 10 g |
| Butter | 110 g |
| Vit A Palmitate | 0.6 g |
| Nonfat Dry Milk Powder-Non Instant | 20 g |
| Whey Protein Concentrate | 25 g |
| Calcium Caseinate-Dispersible EX | 22 g |
| Milk Protein Concentrate | 40 g |
| Butter Buds Blue Cheese Flavor | 65 g |
| Maltrin M100 Maltodextrin GP | 40 g |
| Water | 250 g |
| Lactic Acid 80% | 7.2 g |
| Salt | 7 g |
| TOTALS: | 1097 g |

Add powder to water, let hydrate 2 hours.
Melt ButterGel.
Melt Butter and oil mixture.
Blend together with Braun hand blender while warm.
Blend powder slurry into ButterGel mixture.
Add acid to pH 4.7.
Cook in microwave to 180° F. (82° C.) (stir often).
Cool while stirring occasionally.

| Curry Powder Paste | |
|---|---|
| Curry Powder | 20 g |
| Butter | 10 g |
| Coconut Oil | 40 g |
| ButterGel 450e 10/02 | 100 g |
| Fibrim 2000 Soy Fiber PT | 10 g |
| Hydrol. Vegetable Protein | 7 g |
| Fermented Soy Sauce Powder | 1 g |
| Black Pepper | 1 g |
| Dehydrated Garlic | 0.5 g |
| White Cake Flour-Enriched-Sifted | 10 g |
| Chicken Broth Base | 2 g |
| Water | 20 g |
| TOTALS: | 221.5 g |

| Half-Fat Butter Spread | |
|---|---|
| Emulsifying dextrin hydrogel 20% solids | 60 g |
| Butter | 114 g |
| Water | 50 g |
| Salt | 1 g |
| TOTALS: | 225 g |

| Paraffin Complex | |
|---|---|
| Emulsifying Dextrin Powder | 15 g |
| Water | 85 g |
| Paraffin | 20 g |
| TOTALS: | 120 g |

Preheat paraffin till melted.
Dissolve dextrin powder in water and heat in microwave to 90° C.
Float melted paraffin on top of hot dextrin solution.
Submerge electric hand mixer in container of dextrin solution and begin mixing to draw paraffin down into dextrin solution. The resulting clathrate of paraffin is water disperable and forms a white milky solution which disperses completely in any quantity of excess water.

| Mashed Potato Cream | | |
|---|---:|---|
| Emulsifying Dextrin Powder | 45 | g |
| Water | 546 | g |
| Nonfat Dry Milk Powder-Non Instant | 54 | g |
| Butter | 100 | g |
| Mono + Diglycerides - Soybean Oil | 15 | g |
| Sodium Stearoyl Lactylate- | 6 | g |
| NaturalButter Flavor | 6 | g |
| Peeled Potato-Cooked | 4250 | g |
| Skim Milk | 0.1 | g |
| Salt | 22 | g |
| TOTALS: | 5044 | g |

Proper use is at 15% of cooked potato weight.
Used at 20% of cooked potatoes, salt to taste (approx 0.5% of potato weight) added additional skim milk 6.5% of cooked potato weight.

| Whipped Cream | | |
|---|---:|---|
| Nonfat Milk Solids | 131.7 | g |
| Butter Oil-anhydrous | 322 | g |
| White Granulated Sugar | 131.7 | g |
| Water | 834.1 | g |
| Emulsifying Dextrin Powder | 14.63 | g |
| Water | 58.54 | g |
| Mono + Diglycerides - Palm Oil | 7.317 | g |
| TOTALS: | 1500 | g |

| Blue Cheese Mild cultured, | | |
|---|---:|---|
| Fleischmann's Corn Oil Mixture | 300 | g |
| Emulsifying dextrin hydrogel 20% solids | 300 | g |
| Nonfat Dry Milk Powder-Non Instant | 10 | g |
| Water | 200 | g |
| Nonfat Dry Milk Powder-Non Instant | 20 | g |
| Whey Protein Concentrate | 25 | g |
| Calcium Caseinate-Dispersible | 18 | g |
| Milk Protein Concentrate | 10 | g |
| Butter Buds Dried Cream Extract | 4 | g |
| Butter Buds Blue Cheese | 24 | g |
| Maltrin M100 Maltodextrin GP | 65 | g |
| Butter | 50 | g |
| Salt | 4 | g |
| TOTALS: | 1030 | g |

| ButteryGel Lite, enzyme | | |
|---|---:|---|
| Emulsifying dextrin hydrogel 20% solids | 250 | g |
| Butter | 217 | g |
| Enzyme Preparation | 0.03 | g |
| TOTALS: | 467 | g |

Enzyme preparation: 3 drops Palatase
Add at 50.3° C.
10 minutes reaction time while agitating intermittently with a Braun hand mixer.
Heat to boiling in a microwave oven set at full power.
Cover with plastic and cool at room temperature.

| ICING, Cream Cheese Low Fat | | |
|---|---:|---|
| Cream Cheese Lite Oct. 15, 2002 v.2 | 5 | lb |
| Emulsifying dextrin hydrogel 20% solids | 1 | lb |
| White Powdered Sugar-Sifted | 5 | lb |
| Nonfat Milk Solids | 0.25 | lb |
| Salt | 0.24 | oz-wt |
| Water | 0.1 | lb |
| Pure Vanilla Extract | 1 | oz-wt |
| TOTALS: | 5184 | g |

| Cheddar Cheese analogue | | |
|---|---:|---|
| Fleischmann's Margarine-Stick | 350 | g |
| Emulsifying dextrin hydrogel 20% solids | 300 | g |
| Cargill Phyto Sterol Ester | 20 | g |
| Vegetable Shortening (Crisco/Fluffo) | 0.01 | g |
| Nonfat Dry Milk Powder-Non Instant | 0.01 | g |
| Water | 250 | g |
| Nonfat Dry Milk Powder-Non Instant | 30 | g |
| Whey Protein Concentrate | 25 | g |
| Calcium Caseinate-Dispersible | 18 | g |
| Milk Protein Concentrate | 40 | g |
| Butter Buds Cheddar EX Cheese | 17 | g |
| Butter Buds Manchego Cheese | 4 | g |
| Butter Buds Parmesan Cheese | 3 | g |
| Butter Buds Romano Cheese | 2 | g |
| Maltrin M100 Maltodextrin GP | 80 | g |
| Lactic Acid 80% | 6.5 | g |
| Salt | 6 | g |
| TOTALS: | 1152 | g |

Add powder to water, let hydrate 2 hours.
Melt Emulsifying dextrin hydrogel 20% solids.
Melt Butter and shortening.
Blend together with Braun hand blender while warm.
Blend powder slurry into ButterGel mixture.
Add acid to pH 4.7.
Cook in microwave to 180° F. (stir often)
Cool while stirring occasionally. Less stirring results in harder cheese.

| Boston Creme Filling, Low Fat | | |
|---|---:|---|
| TruSweet 42 High Fructose Corn Syrup | 1.5 | lb |
| 43/62 DE CSU Corn Syrup | 3.234 | lb |
| Emulsifying dextrin hydrogel 20% solids | 1.25 | lb |
| Butter | 100 | g |
| Water | 1 | lb |
| Two Fold Vanilla Extract | 4.256 | g |
| Salt | 20.57 | g |
| Nonfat Milk Solids | 107.8 | g |
| TOTALS: | 3401 | g |

| Butter-oil Clathrate | | |
|---|---:|---|
| Emulsifying dextrin hydrogel 20% solids | 120 | g |
| Water | 150 | g |
| Butter Oil Anhydrous | 180 | g |
| Potassium Sorbate | 0.8084 | g |
| TOTALS: | 450.8 | g |

| Low Fat Ice Cream with Whey Cream | | |
|---|---:|---|
| Emulsifying dextrin hydrogel 20% solids | 75 | g |
| Water | 250 | g |
| Cream-Medium (25%) Fat | 300 | g |
| White Granulated Sugar | 85.51 | g |
| Maltrin M200 Corn Syrup Solids GP | 57.56 | g |
| Ice Cream Stabilizer | 3.289 | g |
| Nonfat Milk Solids | 95.38 | g |
| White Granulated Sugar | 85.51 | g |
| Maltrin M200 Corn Syrup Solids GP | 57.56 | g |
| Ice Cream Stabilizer | 3.289 | g |
| Nonfat Milk Solids | 95.38 | g |
| Water | 522 | g |
| TOTALS: | 1630 | g |

| Perstearic Acid | | |
|---|---:|---|
| Emulsifying dextrin hydrogel powder | 355.5 | g |
| Water | 1421 | g |
| Stearic Acid | 284.4 | g |
| Hydrogen Peroxide 35% | 97.2 | g |
| TOTALS: | 2158 | g |

The dextrin is arbitrarily set at 125% of the stearic acid weight to make the powder more soluble. One mole of stearic acid (284.4 g) to one mole of $H_2O_2$ (34.0 adjusted to 35% solution=97.2 g).

| Co-Dried ButterGel/Low DE MD | | |
|---|---|---|
| Emulsifying dextrin hydrogel 20% solids | 500 g | 83.33% |
| Maltrin M040 Maltodextrin | 100 g | 16.67% |
| TOTALS: | 600 g | 100% |

| Lactylate Hydrate | |
|---|---|
| Emulsifying dextrin hydrogel 20% solids | 45.9 g |
| Water | 16.7 g |
| Sodium Stearoyl Lactylate-Emulsifier | 18.7 g |
| Mono + Diglycerides - Palm Oil | 18.7 g |
| TOTALS: | 100 g |

| Butter Cheese | |
|---|---|
| Emulsifying dextrin powder | 5.88 g |
| Water | 24.3 g |
| Phosphoric Acid MNS | 0.4 g |
| Baking Soda/Sodium Bicarbonate | 0.26 g |
| Butter | 9.15 g |
| Butter | 8 g |
| Salt | 0.8 g |
| Disodium Phosphate Dihydrate-DSPD MNS | 0.4 g |
| Sodium Hexametaphosphate (Graham's Salt) | 0.4 g |
| Dry Curd Cottage Cheese | 100 g |
| TOTALS: | 149.6 g |

| Mashed Potato Cream | |
|---|---|
| Emulsifying Dextrin | 45 g |
| Water | 546 g |
| Nonfat Dry Milk Powder-Non Instant | 54 g |
| Butter | 100 g |
| Mono + Diglycerides - Soybean Oil | 15 g |
| Sodium Stearoyl Lactylate-Emulsifier AI | 6 g |
| Hi Concentrate NC-NaturalButter FlavorCU | 6 g |
| Skim Milk-No Added Vit A | 350 g |
| Peeled Potato-Cooked | 4250 g |
| Skim Milk-No Added Vit A | 0.1 g |
| Salt | 22 g |
| TOTALS: | 5394 g |

| Butter, ½ Fat | |
|---|---|
| Emulsifying dextrin hydrogel 20% solids | 234 g |
| Citric Acid Anhydrous | 0.125 g |
| Lactic Acid 80% | 0.4 g |
| Butter Oil-anhydrous | 156 g |
| Tenox TBHQ Antioxidant EK | 0.1 g |
| Salt | 1.4 g |
| Butter Buds 32X-Flavor Concentrate CU | 0.6 g |
| Butter Buds 32X-Flavor Concentrate CU | 0.6 g |
| Water | 13 g |
| Sweet Buttermilk-Dried | 6 g |
| Potassium Sorbate | 0.4 g |
| TOTALS: | 412.6 g |

| Cream Cheese Lite | |
|---|---|
| Cream Cheese | 600 g |
| Emulsifying dextrin hydrogel 20% solids | 600 g |
| Guar Gum AQ | 1 g |
| Butter | 0.1 g |
| Whey Protein Concentrate | 80 g |
| Water | 120 g |
| Lactic Acid 80% | 0.4 g |
| Salt | 7 g |
| TOTALS: | 1408 g |

| Cream Cheese, ⅓ Less Fat | |
|---|---|
| Cream Cheese | 500 g |
| Emulsifying dextrin hydrogel 20% solids | 250 g |
| Water | 40 g |
| Whey Protein Concentrate | 25 g |
| Lactic Acid 80% | 0.15 g |
| Salt | 2.5 g |
| TOTALS: | 817.6 g |

Melt Emulsifying dextrin hydrogel 20% solids. Add whey to water (Grande Bravo/500) Heat cheese to 70° C., microwave 4 or 5 times at 30 sec, stir between times, pour complex into cheese, while blending, pH 4.9, use 4 drops of 88% lactic acid to bring to 4.8. A homogenizer could be used, possibly at a cooler temprature, for firmer texture.

| Cream Cheese, Pumpable | |
|---|---|
| Cream Cheese | 400 g |
| Butter Oil-anhydrous | 100 g |
| Emulsifying dextrin hydrogel 20% solids | 250 g |
| Water | 150 g |
| Potassium Sorbate | 0.2 g |
| Salt | 7 g |
| Hi Concentrate-Natural Butter Flavor CU | 0.1 g |
| Lactic Acid 80% | 0.2 g |
| TOTALS: | 907.5 g |

Cook dextrin, reserve ⅓, hydrolyze ⅔, denature enzyme with heat (3× to boiling), recombine, add at 85° C. to room temperature cream cheese, blend at low speed, adjust the pH to 5 with malic acid & lactic acid.

To make cheesecake, blend ⅓ Improver with ⅔ cream cheese at room temperature.

Universal Old Fashioned Butter 4-6 drops.

Lactic Acid 10 drops.

Salt 8 grams.

Hydrolyze with Ban 5 minutes+2 minutes after some stirring dropwise (5 drops in 10 grams $H_2O$).

Made with good dextrin

| Cream Filling Butter Gel | |
|---|---|
| White Powdered Sugar-Sifted | 1242 g |
| Nonfat Milk Solids | 104.4 g |
| Salt | 9 g |
| Two Fold Vanilla Extract VD | 9 g |
| TruSweet 55 High Fructose Corn Syrup | 756 g |
| Emulsifying dextrin hydrogel 20% solids | 790 g |
| Vegetable Shortening (Crisco/Fluffo) | 846 g |
| Mono + Diglycerides - Palm Oil | 1 g |
| TOTALS: | 3757 g |

Mix first 4 ingredients.

Pre-blend water and corn syrup and add.

Add shortening, mix ½ minute slow, 4½ minutes medium

Add water slowly, ½ minute.

The Enzymes

Transglutaminase, supplied by Ajinomoto, is an enzyme with the ability to cross-link proteins through the formation of covalent bonds. The two amino acids that it uses to cross-link are glutamine and lysine. These two amino acids are normally found in the casein structure of cheese curd and therefore the effect is synergistic. In other words, the use of the transglutaminase enzyme strengthens the cheese by magnifying or increasing the intermolecular linkages in the existing proteins. This results in a magnification of stretchiness.

Novozym 771 is a liquid preparation of glucose oxidase (EC 1.1.3.4) containing catalase (EC 1.11.1.6). It catalyzes the oxidation of glucose to gluconic acid (a GRAS organic acid with a neutral taste) and removes oxygen simultaneously according to the reaction scheme:

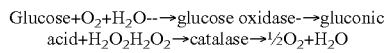

The overall reaction is:

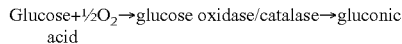

Novozym 771 is produced by a selected strain of *Aspergillus niger* microorganism containing an amount of catalase activity. The enzyme blend causes the oxidation of free sulfhydryl groups, whereby disulfide linkages are formed resulting in stronger, more elastic cheeses.

It has now been found that this mechanism may be used in cheese systems. The proteins that are normally remaining in cheese curds are relatively low in sulfhydryl groups, these groups having been washed out with the soluble whey portion of the process. By adding variable amounts of these whey products back into the cheese mass, either dried and reconstituted with water, or in their original wet form, or concentrated provides a sulfhydryl content to provide an additional functional component to the cheese matrix. Additionally, a lactase enzyme may be added to convert some of the indigenous lactose into additional glucose, which then can fuel the glucose oxidase activity. The action of the catalase enzyme on the byproduct hydrogen peroxide then serves to oxidize the sulfhydryl groups to form disulfide linkages.

These disulfide linkages are in addition to the normally existing linkages that bind caseins. They act as an additional scaffolding of structure that stabilizes the protein mass. This additional structure inhibits the flex of the protein structure and thereby inhibits the flow and stretch characteristics of cheeses at higher temperatures. This is useful for the manufacture of cheeses where decreased flow properties of hot cheese are desirable.

Palatase is a fungal lipase produced by fermentation of a strain of *Rhizomucor miehei* and is used to hydrolyze fatty acids and produce enhanced flavors in cheeses. Normally the enzyme takes a longer period of time to act on the relatively large globules of fat present in young cheese. The internal portions of the fat globules are hidden and not available to the action of the enzymes. It is only after aging, as the naturally occurring proteases shorten the chain lengths of the proteins, that the lipase enzymes can attack the fat component more aggressively and produce the characteristic flavored cheeses. The technology of the present invention divides the fat globules earlier and makes the fat more susceptible to enzymatic attack sooner and to a much more significant degree. In this way, the flavors can be developed much more quickly and economically. The enzymes are then denatured during the cooking process.

Lactozyme is a beta galactosidase (lactase) produced from the yeast *Kluyveromyces fragilis*, which converts lactose to glucose and galactose. These sugars do not brown as much as lactose upon heating and therefore the enzyme can be used to reduce the excess browning that may occur with the higher lactose content associated with higher whey concentration.

Ban 480L is an alpha-amylase produced from *Bacillus amyloliquefaciens* 1,4-alpha-D-glucan glucano-hydrolase. It is an endo amylase attacking the 1-4 bonds along the starch chain internally in a random fashion, but is unable to cleave 1-6 bonds that attach amylopectin branches to the amylose molecule. Thus, the amylopectin branches provide natural built-in barriers to complete hydrolysis and therefore help to maintain a useful minimum size of dextrin end product. (The acetyl groups also have a similar effect). This is contrasted to beta amylases, which are exo-amylases that cleave off maltose units in a step-wise fashion from the ends of starch chains and destroy the hosting capability of the amylose.

Pullulanase enzymes, such as Promozyme from Novo, cleave alpha 1-6 bonds in amylopectin and may be used to de-branch the amylose enzyme to remove the 1-6 linkages and allow the alpha amylase more complete access to the amylose molecule.

In view of the many changes and modifications that can be made without departing from principles underlying the invention, reference should be made to the appended claims for an understanding of the scope of the protection to be afforded the invention.

What is claimed is:

1. A method for producing an amylose starch composition comprising the steps of:
   (A) stirring for at least 3 hours a slurry of about 35 percent solids of starch, the starch having a C-type crystallinity, in water at a temperature from about 20° C. to about 48° C. with a sufficient concentration of a base to obtain a pH of about 10;
   (B) cooling the slurry to a temperature between about 10°C. and 15° C.;
   (C) adding an esterification agent while maintaining a pH of about 8.3 and a temperature from about 10° C. and about 15° C. until a degree of substitution from about 0.08 to about 0.15 is obtained;
   (D) washing the starch with water to remove salts of the esterification agent;
   (E) diluting the starch, while adjusting the pH to about 5.8, to obtain a solids slurry of about 20 percent;
   (F) heating the slurry to a temperature from about 82° C. to about 105° C. for about 2 to about 5 minutes;
   (G) cooling the slurry to between about 50° C. to about 85° C.;
   (H) adding from 1.8 to 10 grams per 770 pounds of starch of a 1,4-alpha-D-glucan glucano-hydrolase to treat the slurry;
   (I) holding the 1,4-alpha-D-glucan glucano-hydrolase in the slurry between about 50° C. and about 85° C. until a desired, lower viscosity is attained;
   (J) heating the slurry to 92° C. to 105° C. to inactivate the 1,4-alpha-D-glucan glucano-hydrolase; and
   (K) cooling the slurry to form a gel, the gel contains sufficient stabilized amylose molecules in a helical configuration to render the gel thermo-reversible.

2. The process of claim 1 wherein the starch is a member selected from the group consisting of pea starch, lentil starch, and mung bean starch.

3. The process of claim 2 wherein the esterification agent is acetic anhydride.

4. The process of claim 1 wherein the base is sodium hydroxide.

5. The process of claim 1 wherein the esterification agent is a member selected from the group consisting of acetic anhydride, propionic anhydride, butyrate anhydride, hexanoate anhydride, and mixtures thereof.

6. The process of claim 1 wherein the 1,4-alpha-D-glucan glucano-hydrolase is a bacterial amylase from *Bacillus amyloliquefaciens*.

7. The process of claim 1 further comprising the step of:

(L) drying the slurry to a powder.

8. A method for producing an amylose starch composition comprising the steps of:

(A) stirring for about 3 hours a slurry of about 35 percent solids of starch, the starch having a C-type crystallinity, in water at a temperature from about 20° C. to about 48° C. with a sufficient concentration of sodium hydroxide to obtain a pH of about 10;

(B) cooling the slurry to a temperature below about 10° C.;

(C) adding acetic anhydride while maintaining a pH of about 8.3 and at a temperature below about 15° C. until a degree of substitution from about 0.08 to about 0.10 is obtained;

(D) washing the starch with water to remove sodium acetate;

(E) diluting the starch, while adjusting the pH to about 5.8, to obtain a solids slurry of about 20 percent;

(F) heating the slurry to a temperature from about 95° C. to about 105° C. for about 2 to about 5 minutes;

(G) cooling the slurry to below about 73° C.;

(H) adding from 1.8 to 10 grams per 770 pounds of starch of a bacterial amylase from *Bacillus amyloliquefaciens*, the bacterial amylase being 1,4-alpha-D-glucan glucano-hydrolase, to treat the slurry;

(I) holding the 1,4-alpha-D-glucan glucano-hydrolase in the slurry below about 73° C. until a desired, lower viscosity is attained;

(J) heating the slurry to 92° C. to 105° C. to inactivate the 1,4-alpha-D-glucan glucano-hydrolase; and (K) cooling the slurry to form a gel, the gel contains sufficient stabilized amylose molecules in a helical configuration to render the gel thermo-reversible.

9. The process of claim 8 further comprising the step of:

(L) drying the slurry to a powder

\* \* \* \* \*

UNITED STATES PATENT AND TRADEMARK OFFICE
CERTIFICATE OF CORRECTION

PATENT NO. : 7,550,279 B2  Page 1 of 1
APPLICATION NO. : 10/902019
DATED : June 23, 2009
INVENTOR(S) : Gary B. Nickel It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 428 days.

Signed and Sealed this

Seventh Day of September, 2010

David J. Kappos
*Director of the United States Patent and Trademark Office*